US012790620B2

(12) United States Patent
Van Ex et al.

(10) Patent No.: US 12,790,620 B2
(45) Date of Patent: Nov. 10, 2026

(54) REDUCED HEIGHT MAIZE

(71) Applicant: INARI AGRICULTURE TECHNOLOGY, INC., Cambridge, MA (US)

(72) Inventors: Frédéric Van Ex, Kortrijk (BE); Hannes Bart Claeys, Ghent (BE)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 18/727,642

(22) PCT Filed: Dec. 22, 2022

(86) PCT No.: PCT/US2022/082208
§ 371 (c)(1),
(2) Date: Jul. 9, 2024

(87) PCT Pub. No.: WO2023/136966
PCT Pub. Date: Jul. 20, 2023

(65) Prior Publication Data

US 2025/0382626 A1 Dec. 18, 2025

Related U.S. Application Data

(60) Provisional application No. 63/266,684, filed on Jan. 12, 2022.

(51) Int. Cl.
*C12N 15/82* (2006.01)
*C12N 9/22* (2006.01)
*C12N 15/11* (2006.01)

(52) U.S. Cl.
CPC ......... *C12N 15/8262* (2013.01); *C12N 9/226* (2025.05); *C12N 15/11* (2013.01); *C12N 15/8213* (2013.01); *C12N 2310/20* (2017.05); *C12N 2800/80* (2013.01)

(58) Field of Classification Search
None
See application file for complete search history.

(56) References Cited

U.S. PATENT DOCUMENTS 6,222,099 B1 4/2001 Gengenbach et al.
7,309,816 B1 12/2007 Bruce et al.
8,030,473 B2 10/2011 Carrington et al.
8,404,928 B2 3/2013 Allen et al.
8,895,818 B2 11/2014 Chomet et al.
10,227,611 B2 3/2019 Doudna et al.
11,174,492 B2 11/2021 Turgeman et al.
11,198,885 B1 12/2021 Claeys
11,976,291 B2 5/2024 Claeys
12,188,031 B2 1/2025 Claeys
2003/0049814 A1 3/2003 Andrews et al.
2012/0227131 A1 9/2012 Abad et al.
2015/0059010 A1 2/2015 Cigan et al.
2015/0082478 A1 3/2015 Cigan et al.
2015/0344912 A1 12/2015 Kim et al.
2016/0138008 A1 5/2016 Doudna et al.
2016/0208243 A1 7/2016 Zhang et al.
2016/0255798 A1 9/2016 Buendgen
2017/0166912 A1 6/2017 Brower-Toland et al.
2017/0183677 A1 6/2017 Gao et al.
2017/0306349 A1 10/2017 Djukanovic et al.
2017/0367383 A1* 12/2017 Esquivel ................. A23L 13/60
2018/0028512 A1* 2/2018 Lee ...................... A61K 9/7038
2019/0352655 A1 11/2019 Niu et al.
2020/0407754 A1 12/2020 Cemák
2021/0324401 A1 10/2021 Abbitt et al.
2022/0090095 A1 3/2022 Higgins et al.
2022/0098605 A1 3/2022 Claeys
2023/0117599 A1 4/2023 Wang et al.
2023/0284585 A1* 9/2023 Wahlquist .............. A01H 6/545
2024/0271154 A1 8/2024 Claeys
2025/0084426 A1 3/2025 Claeys

FOREIGN PATENT DOCUMENTS

CN 102234330 A 11/2011
CN 106191080 A 12/2016
WO 2018076335 A1 5/2018

OTHER PUBLICATIONS

Cassani et al. Characterization of the first dominant dwarf maize mutant carrying a single amino acid insertion in the VHYNP domain of the dwarf8 gene. (2009) Molecular Breeding; vol. 24; pp. 375-385 (Year: 2009).*
Merriam-Webster Definition of "about" (2018) on the world wide web at www.merriam-webster.com; downloaded on Apr. 13, 2018; p. 1 (Year: 2018).*
Murray et al. Simple and accurate transcriptional start site identification using Smar2C2 and examination of conserved promoter features. (2022) The Plant Journal; vol. 112, pp. 583-596 (Year: 2022).*
Ellis et al. The ocs element: a 16 base pair palindrome essential for activity of the octopine synthase enhancer. (1987) The EMBO Journal; vol. 6; pp. 3203-3208 (Year: 1987).*
Alexandrov et al. "Insights into corn genes derived from large-scale cDNA sequencing." Plant molecular biology 69.1 (2009): 179-194.
Bortesi et al. "The CRISPR/Cas9 system for plant genome editing and beyond." Biotechnology advances 33.1 (2015): 41-52.
Database MaizeGDB: Zm00001d031079, MaizeGDB: Maize Genetics and Genomics Database, Gene Model Set: Zm00001d.2. Retrieved from the Internet: <URL: https://www.maizegdb.org/gene_center/gene/Zm00001d031079#overview>, 7 pages.
Davey et al. "Deconstruction of complex protein signaling switches: a roadmap toward engineering higher-order gene regulators." Wiley Interdisciplinary Reviews: Nanomedicine and Nanobiotechnology 9.6 (2017): 1-15.

(Continued)

*Primary Examiner* — Cathy Kingdon
(74) *Attorney, Agent, or Firm* — McKee, Voorhees & Sease, PLC

(57) ABSTRACT

Modifications of maize genes Zm1d31079 and Zm1d44812 which provide maize plants with reduced height are disclosed. Maize plants comprising a modified Zm1d31079 or Zm1d44812 with a heterologous enhancing element are described. Also disclosed are seed obtained from such plants as well as use of the seed and plants to produce commodity productions and in maize breeding.

15 Claims, 11 Drawing Sheets

Figure 3:
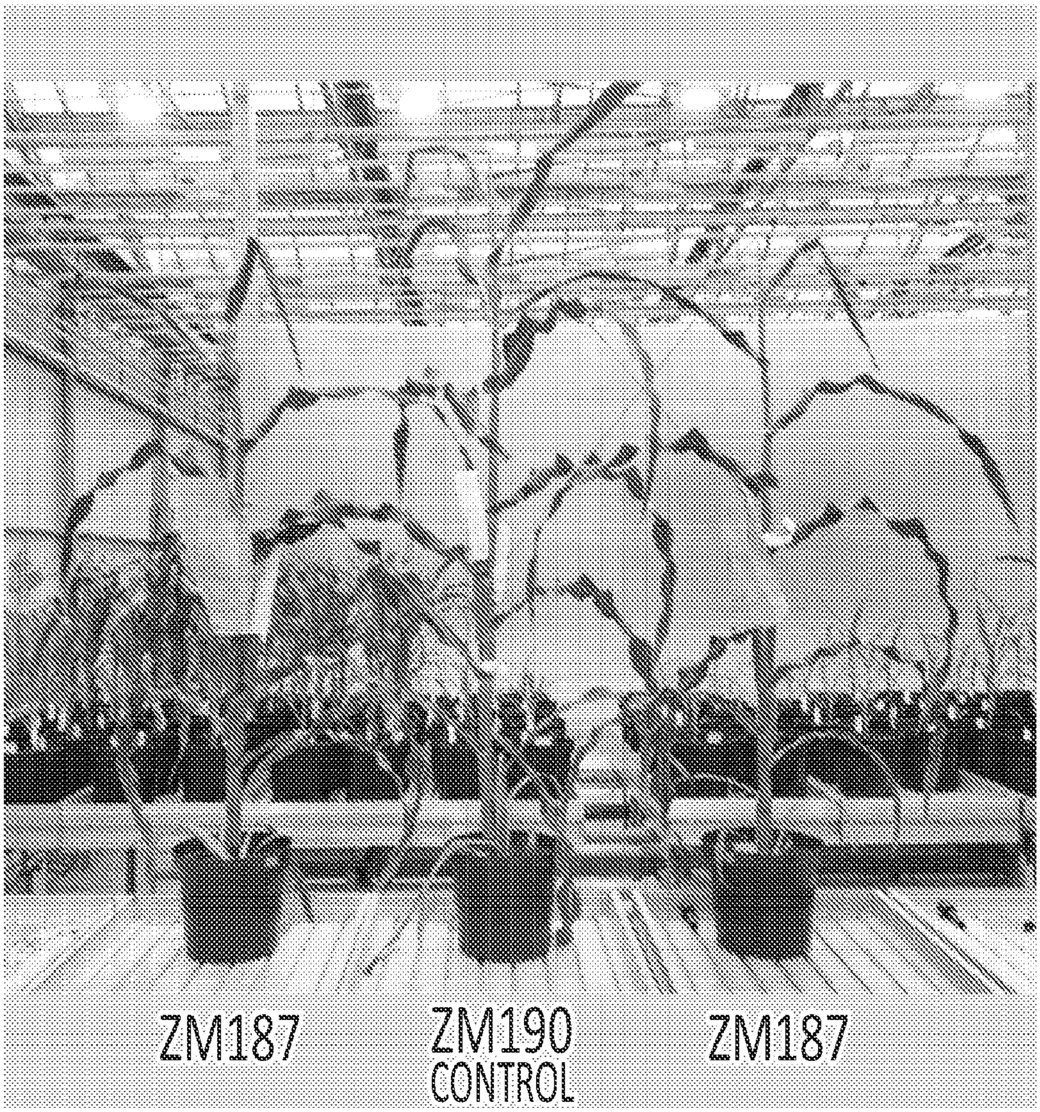

Specification includes a Sequence Listing.

(56) References Cited

OTHER PUBLICATIONS

Ellis et al. "Does the ocs-element occur as a functional component of the promoters of plant genes?." The Plant Journal 4.3 (1993): 433-443.
Ellis et al. "The ocs element: a 16 base pair palindrome essential for activity of the octopine synthase enhancer." The EMBO Journal 6.11 (1987): 3203-3208.
Extended European Search Report in EP21873582.7, mailed Jul. 26, 2024, 7 pages.
Fiering et al. "Single cell assay of a transcription factor reveals a threshold in transcription activated by signals emanating from the T-cell antigen receptor." Genes & development 4.10 (1990): 1823-1834.
Gardiner et al. "Anchoring 9,371 maize expressed sequence tagged unigenes to the bacterial artificial chromosome contig map by two-dimensional overgo hybridization." Plant Physiology 134.4 (2004): 1317-1326.
Gómez-ariza et al. "A transcription factor coordinating internode elongation and photoperiodic signals in rice." Nature plants 5.4 (2019): 358-362.
International Search Report and Written Opinion in PCT/US2022/072963, mailed Nov. 16, 2022, 18 pages.
International Search Report and Written Opinion in PCT/US22/82208, mailed Apr. 18, 2023, 10 pages.
Invitation to Pay Additional Fees in PCT/US2022/072963, mailed Sep. 16, 2022, 3 pages.
Laxa, M. "Intron-mediated enhancement: a tool for heterologous gene expression in plants?." Frontiers in Plant Science 7 (2017): 1-13.
Office Action in U.S. Appl. No. 17/249,437, mailed Apr. 30, 2021, 11 pages.
Office Action in U.S. Appl. No. 17/249,437, mailed Sep. 28, 2021, 7 pages.
Parra et al. "Comparative and functional analysis of intron-mediated enhancement signals reveals conserved features among plants." Nucleic acids research 39.13 (2011): 5328-5337.
Rose, A. "The effect of intron location on intron-mediated enhancement of gene expression in *Arabidopsis*." The Plant Journal 40.5 (2004): 744-751.
Singh et al. "Saturation mutagenesis of the octopine synthase enhancer: correlation of mutant phenotypes with binding of a nuclear protein factor." Proceedings of the National Academy of Sciences 86.10 (1989): 3733-3737.
Sugio et al. "The 5'-untranslated region of the *Oryza sativa* alcohol dehydrogenase gene functions as a translational enhancer in monocotyledonous plant cells." Journal of bioscience and bioengineering 105.3 (2008): 300-302.
Ulmasov et al. "Aux/IAA proteins repress expression of reporter genes containing natural and highly active synthetic auxin response elements." The Plant Cell 9.11 (1997): 1963-1971.
Wilson et al. "The lactose repressor system: paradigms for regulation, allosteric behavior and protein folding." Cellular and molecular life sciences 64.1 (2007): 3-16.
Xiao et al. "Cis and trans determinants of epigenetic silencing by Polycomb repressive complex 2 in *Arabidopsis*." with Supplementary Material, Nature genetics 49.10 (2017): 1-42.
Yamasaki et al. "Identification of 5'-untranslated regions that function as effective translational enhancers in monocotyledonous plant cells using a novel method of genome-wide analysis." Plant Biotechnology 35.4 (2018): 365-373.
Cassani et al. "Characterization of the first dominant dwarf maize mutant carrying a single amino acid insertion in the VHYNP domain of the dwarf8 gene." Molecular Breeding 24.4 (2009): 375-385.
Extended European Search Report in EP22920975.4, mailed Nov. 25, 2025, 9 pages.
Hufford et al. "De novo assembly, annotation, and comparative analysis of 26 diverse maize genomes." Science 373.6555 (2021): 655-662.
MaizeGDB BLAST: ALL NAM Founders, Datasheet [online], MaizeGDB: Maize Genetics and Genomics Database, 2026. Retrieved from the Internet: <URL:https://www.maizegdb.org/BLAST/BLAST_run.php?job_id=tqWkBRCox8nP>, 49 pages.
Office Action in CN202280087805.7, mailed Jun. 30, 2026, 14 pages.
Office Action in EP22920975.4, mailed Jul. 20, 2026, 6 pages.

* cited by examiner ggataaatagggattggagtggattgaagtgtattttaggtattgaaagggaaattagttta
tattacacttcaatacaccttataccacctcaatccactccaatccaagattacccaaacaa
accctaagggcttgttcgctttggagtggattgaggggattggaggggattaaatcccctc
ctatacaaatttgtataggaggggatttaatcccctccaatccccctcaatccactccaaag
cgaacaagccctaaggggattggaggggattcaatccccttctatataaatttgtatagaa
gtggattgaatcccctctaatccccctcaatccactcctaaccgaacagggccttaggggtg
gtgacatacgtgtcccctccccgctaagaagtggcactgacccctactcaatctacatgggc
tttttaacctcacttcctcccacgtcgcgaccgagatcctggctaccaacaactttcacgct
attcaatctacatggttcttgtgtccatgagggattatgggaaggagagatagatttgttta
taatcgaagggagaaggggagtgccattgcattatatctagatacatatatacatataataa
taatgcatttgaaaaggccaaaccctcgatcgtgtaattcaaaacaaagatagtactatact
atatatatgcatgtcatggctctccagcagtttacccatcctatctcctcctatatcatatt
cgacttcaaatttcactcagtcaacaacagtacaggctatgatgcaaaacattgcgggcagt
ctaatagctacacatatgggacaccatacccacaccaagaatcgtctcattctttttttctta
actcggaactacattaatgagttcccaacttgcaactctcttgtgaagtttcagtgctcttt
caatgacgtgaactgttctcgctccgaaaggaggaagctgataacgaggagagcccatcata
accggttggagtaagcaaccaaactcgatcagcatcatggggtcaccatcactcggtaacca
aattgctctcgagctaagctagctagcttgttgcaagatcgagtcgtcatgcaaacttcgag
cttggcttgggcgtcttgttaacagactttccccactgtttcccacgacctcactctaattg
gatgcacacaagttataataatgcatatatagatatagatatatctggctgtttagactgct
gcagcgctatagctaaggaaatgtatgtagataaaaggcgcacacatatatttgaacggcat
atgttaataaaactacctcctgtattttctttctttctttttcaatatatatgtcgaaggaa
atggtgccgtggaacgtccgacacgacatgtggagggagctgcagcgctacagcaacgcata
tacgcgcaccatgagtgtgatgttgattagcgccaccgtaccaccacctgtgatctctgtgg
cagtatatataatataatataatataatataatataatataatataatataatataatataa
tataatataatataataatcacccccccatgcatgcagccagcttttggttttcgggcgccaa
aatgagcctgcgtgcttgtcgtcttcctgcaggccccttgcttgccctgccctcatggcggt
tgcccaaacagcgcgggggcgggggcgggccccgccgctgccagttcgccgcttcaataat
taatgcagcgtcggaattggggcgtggtgggcttgccatttctgatttctgcacctgcttct
gccacatggccgtcgtcgtaacctccttctcctcctcctaaagctagctagctagctagtac
tcgtgtacctgcaagtgttatatagtaggagtagcacctcctccaccaatcgcgcgcacaca
cacacccagcttagctcagctcaggtagctatagctagagagctggacgaccctcgcgcgac
ctcagatagattttttaATGGAGGCGCCAGCAGCGCCACCTCCGTCGTACGACGGCGGCGGCG
GCGGCGGCTACGTCCTCGTCGACCTGTCCCTGACGCTGGGCCCGACCGCGACGCCACACCCT
GCCTCCTCCTCCTCTCCTGAGCCTGACCACACACCAGCCGCCGCCGCCGCCGGTTCCAGTTC
CGCCGGCGTGCGGCTGTTCCCGTGCCTCTTCTGCAACAAGAAGTTCCTCAAGTCGCAGGCGC
TCGGCGGCCACCAGAACGCGCACAAGAAGGAGAGGAGCGTGGGGTGGAACGCCCACCTCTAC
CTCCCGCCGCCGGCCGCGGACACGGCGTCGGCGTCGGTCGCCGGCGGCGCCGCCGCTCGTGC
CGCGACGACGCCCGTCGGCAGCAGCCACGCGCTGCCGATGATCCAGGCCGTCTCGCACTCGT
GCCACCACCATGAGCACCACCACCGGGACGGCGGCGCGGCGGCGCCGTTGTTGGAGACGGCG
TGGTGGTCGTCGTGCGCGGAGGAGAAACAGCAGAGGCACCCCGTTGACCTCAATCTCAGGCT
CTAG*ctgctagcgctgtcatatcccctgcttgtgtgcgtaatatataaatcctgaaggagta*
*cgtaacgtaccgtacgtgctgtcgaggtagggtgaggcgtctcggtgtgcctgtgcaaaagc*
*gtgcgaggcccatgggccatggcccagcattctatgattatgtgtcgtcgcaacgagcacgc*
*acactttatagttttatggtgccaattatatgcctctttatttca*

FIGURE 1 gtgacttgagagagagtgtgtgttccgtgtgttatttgtcgctcttgtcgcttggcttttgc
aatcgtgctttcttccttcccattcttattctcaaggcacttgtaatcaaagcaagagacac
taagtttgtagtggtccttgtggggtctaagtgacccatttgattaaggagaaagctcactc
ggtctaagtgaccgtttgagagagggaaagggttgaaatagacccggtctttgtgaccacct
caacggggagtaggtttgcaagaaccgaacctcggtaaaacaaatcatcgtgtcttgctctt
tatttgctcacgatttgttttgcgccctctctctctcggactcgtctatatttctaacgcta
acctgacttatagttgtgcttaagtttataaatttcagatttgccttattcacccccctct
aggcgactttcagcgcggtactgcggcgacgtaggaaatttggcgagaaattgtcgttgctg
caattagtttccatgcccaggaatccagcgagcaccatccggtagacactgtgagctccaat
gaagcttttcgggaccgaaacgacatcaagggcacggatcggcgatcacggtctcttcctct
gttatcgcggcggcattcactcgcccacccttacggcaatggtacccttgggccaccggttc
atcgtgatgcaagatggatgagaggggggggtgcacgactaggagttatatatcctaggatc
tagctcaaatccgagcggtgctagccagatcggagaagaacacgacagagtttgttaccggc
aaagggacccacgtccaacgatccatgagcacgcgatgcactcaaaggctacgggcgggtcc
cactggttggtcttagccggatcatgggtgcgcgatgcatcggcgaccgcttcctttcgtgt
ggggaggctgggtccgcggacgaagaagtggaggtgggccgggtagcggcccacacgggcga
ggggaaggaaaacagaattgggctatggaggaaggttttggcccagccagctgtttccttat
tttttattgatttctgttttaaattttcaactttaaattcaaatctcgaatttcaaattgta
tttgggtggaaaactagaatctagataaatgcacaatcaaataaatactcaacatgatgcat
atttctatttatatatttttatagtaattgtttaatcctttttggttaaataacatgcttcga
aatatgccatacaacaattttcagttttgaagaaatattaatttaaacctatagtcaaatga
aaggtttatccaagatttattaattgtttgttgtaataggagatatatatattctccaatta
caaggtgcttttgacttaaccttatttagagaaggttttctagtcatacaattcatcaatta
ttaattgtagacatccctgctttatttctttgagaaaataaaacctaatttcctagggttaa
atataataatttttttagatcactatttatccaaaaaaatcattgttatagatatttttaatta
ttgtttttgaagaaatatttataaattccaaaataaaattttggatgttacgttggtgcact
ggcctgggccacgcaccttgctaaaccggcctgggccgatttctttgttccccgcacaata
taatcacgagcataggctggcctcactcgtctctaaacaggccggttctcttcaaacatcgt
aatttgaccccaaattggatccctttcatttatatatgatgttttaatccgacttttgact
tccagattattttttgctgtcaacaatcctagctccagctgtcatttatccaaaggtttatg
gtggcagatcttaacggctggcatacgtgcagaatttctcctttctttacagttacacccct
cccctccccctcgtgtcggggagtgtgcagtgcacatctgatgtgtataaataatcacacgc
acctatgcccactccacctcccgcgttcctccactccacggctcccccaccccactcatcac
actctcccaccgcacctcgccgccgcggggcaccgcgccataaagtgcgttcccggctgcac
ggacgtcgaggagcagctcgcaagtgtttcttggtgcgtcgatcggcaagATGatcaccggc
acggacttctaccacgtcatgacggccatggtgccgttgtacgttgccatgatcctggcgta
cggatccgtcaggtggtggcgcatcttcacgccggaccagtgctcggggatcaaccgcttcg
tggcgctcttcgccgtgccgctgctgtccttccacttcatctccaccaacaacccctacacc
atgaacatccggttcatcgccgccgacacgctgcagaagctgatcgtcctggcgctgctcac
tgcatggagctacctctcccgccggggctgcctcgagtggaccatcacgctcttctccctgt
cgacgctgcccaacacgctggtgatgggcatcccgctgctcaagggcatgtacggcgacttc
tccggcagcctcatggtgcagatcgtggtgctccagtgcatcatctggtacacgctgatgct
gttcatgttcgagtaccgcggcgccaggatcctcatcaccgagcagttccccgacacggcgg
gcgccatcgcctccatcgtggtggaccccgacgtggtgtcgctggacgggcgcaacgacgcc
atcgagacggaggccgaggtgaaggaggacggcaagatacacgtcaccgt

FIGURE 2A gcggcgctccaacgcgtcgcgctcggacatctactcccggcggtccatggggttctccagca
ccacgccgcggcccagcaacctgaccaacgccgagatctactcgctgcagtcgtcgaggaac
cccacgccgcggggctccagcttcaaccacaccgacttctactccatggtcggccgcagctc
caacttcgccgccggggacgcgttcggcctgcgcacgggcgccacgcccaggccgtccaact
acgaggaggacccgcagggcaaggcgaacaagtacggccagtacccggcgcccaacccggcc
atggcggcgcagcccgccaagggcctcaagaaggcggccaatgggcaggccaagggcgagga
cggcaaggacctacacatgttcgtgtggagctccagcgcgtcgcccgtgtccgacgtgttcg
gcaatggcgccgccgagtacaacgacgcggccgccgtcaaggaggtccgcatggccgtcgcc
tccccgcgcaaaggtagcttctcctcgttttggcttttgagctccttccttcctgctttgg
ctgcgctgcatgctcagacacacacctgttctgttcttgttggacgttttagttgcggcgga
cgggaggaaggagcggggcgaggacttcgcggagcgggacgacttcagcttcgggaacaggg
gcgcggcggagagggacgcggaagccggcgacgagaaggcggcggcggcggctgcggctgcg
caggggaatgcaggcgccgtggcggcgcccgcggcgatgccaccgacgagcgtgatgacgcg
gctgatcctcatcatggtgtggcgcaaactcatccgtaaccccaacacctactccagcctca
tcggcctcatctggtcgctcgtctgcttcaggtaaccagcgtcaccggcgcggcgtgcttga
aattagtagtgggcgttgcatctttcgctaacctgtttcgtttctggacacgaacgcatacg
caggtggaacttcgagatgccggcgatcatcctcaagtccatctcgatcctctccgacgccg
ggctcggcatggccatgttcagcctcggtccgtggatctcaaaaccctctctgctgcctcct
ctgtctggagtcgcatcgccacgccacctatggaacagttaaccccccttgtactgacaccgc
gcgtgacgtcgccttcctccgtgcagggctgttcatggcgctgcagccacggataatcgcgt
gcgggaacaaggtggccacgttcgccatggccgtgcggttcctgaccggcccggccgtcatg
gccgccgcctcctttgccgtcggcctccgcggcacgctcctccacgtcgccatcgtccaggt
aaaaactctccgaaccgaaccgaaccaaaccaaccaaccgcacaaacaaacccactggcagg
cacgcacgccactgacaagggccgcaccgccttttgagaaagagatgaaaaaaaatatatcc
aagcacaagcagcggtcaagtggccggccgggcatgccgatcgatatgccccctgtgccggt
aaagcgcggcacagcctcctttcgcttttggactttgcacgcacaacacaaattcgcccttt
tttttgttgccccccccccccccccccccccccccctcgccgcctctgccactgactgac
gttcgttttgtttactgacgacgcacgcaggccgcgctgccgcagggcattgtccccttcgt
gttcgccaaggagtacggcgtgcaccctgacatcctcagcacggcgtaagcaacgcagcctt
tgtgttccatccgtcttgctcttgcttgcatgcagctgagctaggcactagcactagcagca
gccagcagcagcagcgccgggattcccgggtctccgcccgctttatttgcctcaggttttt
tttttgtctcacctgctgtcggctttgcttcgtcgtggtgttgcagagtcatcttcggcatg
ctcatcgcgctgcccatcacgctggtgtactacatcctgatggggctgtgaaaaagccagac
aagctgctcgttcccgcaggccaacagcgatgccggatggggatgtggagcaggaggagaca
gactagggggacaagacaactgcgcaggggcaggggcgggggcgggggcggcaggttaat
tcgtaggagtatgcttttaggtgtagacatcatggaacgcgattagagagcaaacaaaaaat
gtttttaggacaaacccaacgtcatatgcaaaaatccttggggtgacagtttgcgttgcaa
agcatccggtcatgagttttgatttgggtgtgttagggacttttcatgcgcatggctttcca
tgccctatataaaatggatgcgtgtcacttcgatggaatgctagggctcttctttcttgttc
atctagggtatatatacttcttggactggcaccacgcatgtccctgcttcagtacttgctta
acagtatctgacatcaaagcgggcgagtggggtgatttggtcgttaatccttcagcatcaaa
cccttgctgtgcaaccgtactagttcga

FIGURE 2B

FIGURE 8
PLANTED IN THE GREENHOUSE ON WEEK 34
ZM 187_1A
ZM 187_1B
ZM 190_1C
ZM 187_1E
ZM 187_1F

REDUCED HEIGHT MAIZE

CROSS-REFERENCE TO RELATED APPLICATIONS

This U.S. patent application is the U.S. national phase of international patent application PCT/US2022/082208 which claims the benefit of U.S. provisional patent application Ser. No. 63/266,684, filed Jan. 12, 2022 and incorporated herein by reference in its entirety.

INCORPORATION OF SEQUENCE LISTING

The sequence listing contained in the file named "P13777US01v2.xml" which is 81,234 bytes (measured in MS-Windows®) and was created on Jun. 26, 2025, is incorporated herein by reference in its entirety. The sequence listing contained in the file named "P13777W000.XML" which is 105,723 bytes (measured in MS-Windows®), comprises 125 biological sequences, and was created on Dec. 1, 2022, was electronically filed and is incorporated herein by reference in its entirety.

BACKGROUND

Plant height is to a large extent determined by stem elongation which is regulated by different factors for example by plant hormones such as gibberellic acid. Reduced plant height is a useful commercial trait linked to improved performance, agronomical practices and overall yield.

A number of genes have been described to be involved in plant height such as *Brevis* plant1 (BV1), brachytic2 (BR2), compact plant2 (ct2) and others. As most of these genes are positive regulators of plant growth, complete or near complete loss-of-function mutations in such genes typically results in severe reductions of plant height which are less useful. Ellis et al., 1987, EMBO J. (6):11:3203-3208, disclose a 16 base pair bacterial octopine synthase gene enhancer element that could increase expression of exogenous genes in maize and tobacco protoplasts in transient expression assays. PCT Patent Application WO 2018/140899 discloses insertion of expression-enhancing elements with homology to the bacterial octopine synthase gene enhancer element in the promoter region of a maize Lc gene in a maize protoplast genome to increase expression of that gene.

SUMMARY

Maize plants comprising a modified Zm1d31079 gene wherein a heterologous expression enhancing element is located in the modified gene, and wherein the unmodified Zm1d31079 gene comprises the DNA molecule of SEQ ID NO: 1 or an allelic variant thereof are provided. Maize plants comprising a modified Zm1d44812 gene wherein a heterologous expression enhancing element is located in the modified gene, wherein the unmodified Zm1d44812 gene comprises the DNA molecule of SEQ ID NO: 8 or an allelic variant thereof, and wherein the modified Zm1d44812 gene is located in the native chromosomal location of the unmodified Zm1d44812 gene are provided. Maize plant parts comprising the modified Zm1d31079 gene or the modified Zm1d44812 genes are also provided. In some embodiments, the maize plant part is a seed, stalk, stem, or leaf.

Methods of producing maize seed, comprising growing any of the aforementioned maize plants of and harvesting seed therefrom are provided. Methods of producing hybrid maize seed comprising crossing an aforementioned maize plant which is homozygous for the modified Zm1d31079 gene to a maize plant homozygous for the unmodified Zm1d31079 gene and harvesting seed from a pollen recipient of the cross, optionally wherein the maize plant homozygous for the modified Zm1d31079 gene is the pollen donor are provided. Methods of producing hybrid maize seed comprising crossing an aforementioned maize plant which is homozygous for the modified Zm1d31079 gene to a maize plant homozygous for the unmodified Zm1d31079 gene and harvesting seed from a pollen recipient of the cross, optionally wherein the maize plant homozygous for the modified Zm1d31079 gene is the pollen recipient are provided. Methods of producing hybrid maize seed comprising crossing an aforementioned maize plant which is homozygous for the modified Zm1d31079 gene to another maize plant homozygous for the modified Zm1d31079 gene and harvesting seed from a pollen recipient of the cross are provided. Methods of producing hybrid maize seed comprising crossing an aforementioned maize plant homozygous for the modified Zm1d44812 gene to a maize plant homozygous for the unmodified Zm1d44812 gene and harvesting seed from a pollen recipient of the cross, optionally wherein the maize plant homozygous for the modified Zm1d44812 gene is the pollen donor. Methods of producing inbred maize seed comprising selfing: (i) a maize plant homozygous for the modified Zm1d31079 gene; or (ii) a maize plant homozygous for the modified Zm1d44812 gene are also provided. Methods of producing hybrid maize seed comprising crossing an aforementioned maize plant homozygous for the modified Zm1d44812 gene to a maize plant homozygous for the unmodified Zm1d44812 gene and harvesting seed from a pollen recipient of the cross, optionally wherein the maize plant homozygous for the modified Zm1d44812 gene is the pollen recipient are provided. Methods of producing hybrid maize seed comprising crossing an aforementioned maize plant homozygous for the modified Zm1d44812 gene to another maize plant homozygous for the modified Zm1d44812 gene and harvesting seed from a pollen recipient of the cross are provided. Methods of producing inbred maize seed comprising selfing: (i) a maize plant homozygous for the modified Zm1d31079 gene; or (ii) a maize plant homozygous for the modified Zm1d44812 gene are also provided.

Methods of producing a maize plant comprising an added desired trait, said method comprising introducing a transgene, a targeted genetic change, and/or a genetic locus conferring the desired trait into any of the aforementioned maize plants are provided.

Methods of producing a commodity maize plant product, said method comprising: (i) processing any of the aforementioned maize plants or a maize seed obtained therefrom; and (ii) recovering the commodity maize plant product from the processed maize plant or maize seed are provided.

Biological samples comprising a detectable amount of a DNA molecule comprising a heterologous transcription enhancer, a heterologous intron, and/or heterologous translational enhancing element located in a DNA fragment of a modified Zm1d31079 gene or in a DNA fragment of a modified Zm1d44812 gene are provided.

Methods of making an aforementioned maize plant, comprising: (a) contacting a maize plant genome with gene editing molecules comprising a first site-specific nuclease which introduces a double stranded DNA break in a promoter region, a 5' UTR, a coding region, a 3' UTR, or a 3' flanking region in: (i) an unmodified Zm1d31079 gene comprising the DNA molecule of SEQ ID NO: 1 or an allelic variant thereof; or (ii) an unmodified Zm1d44812 gene comprising the DNA molecule of SEQ ID NO: 8 or an allelic variant thereof, and a donor DNA template or other DNA template comprising a heterologous expression enhancing element; and (b) selecting a maize plant comprising a modified Zm1d31079 gene or a modified Zm1d44812 gene, wherein the modified Zm1d31079 gene or the modified Zm1d44812 gene comprises an insertion of the heterologous expression enhancing element in the promoter region, the 5' UTR, the coding region, the 3' UTR, or the 3' flanking region of the gene, wherein expression of the modified Zm1d31079 gene or a modified Zm1d44812 gene is increased in at least one tissue, and wherein height of the maize plant comprising the modified Zm1d31079 gene or the modified Zm1d44812 gene is decreased in comparison to a control maize plant lacking the modified Zm1d31079 gene or the modified Zm1d44812 gene are provided.

Methods of making an aforementioned maize plant, comprising: (a) contacting a maize plant genome with a transgene comprising a modified Zm1d31079 gene, wherein the modified Zm1d31079 gene comprises a heterologous promoter, heterologous 5' UTR, and/or heterologous intron which is operably linked to a coding region encoding the Zm1d31079 protein of SEQ ID NO: 2 or an allelic variant thereof or; and (b) selecting a transgenic maize plant comprising the modified Zm1d31079 gene, wherein expression of the modified Zm1d31079 gene is increased in at least one tissue and wherein height of the maize plant is decreased in comparison to a control maize plant lacking the modified Zm1d31079 gene are provided.

BRIEF DESCRIPTION OF THE DRAWINGS/FIGURES

FIG. 1 depicts an unmodified maize Zm1d31079 gene sequence (SEQ ID NO: 1). The location of guide RNA recognition sites in the promoter are shown in bold, the 5' untranslated region (5'UTR) is underlined, the coding region is in upper case, and the 3'UTR and 3' flanking region are italicized.

FIGS. 2A and 2B depict an unmodified maize Zm1d44812 gene sequence (SEQ ID NO: 8). The location of guide RNA recognition sites in the promoter are shown in bold, the 5' untranslated region (5'UTR) is underlined, the ATG translation initiation codon is in upper case.

FIG. 3 shows two "T Zero" (T0) ZM187 genetically edited maize plants comprising a transcription enhancer inserted in the Zm1d44812 gene promoter and a T0 ZM190 control plant lacking the transcription enhancer insertion. The T0 ZM187 genetically edited maize plants were generated with a Cas nuclease, a Zm1d44812_Pro-75 gRNA comprising an RNA encoded by SEQ ID NO: 10, and a triplicated ZmOCS enhancer element donor DNA (SEQ ID NO: 18).

Figure 4:

FIG. 4 shows two "T Zero" (T0) ZM200 genetically edited maize plants comprising a transcription enhancer inserted in the Zm1d31709 gene promoter and a T0 ZM194 control plant lacking the transcription enhancer insertion. The T0 ZM200 genetically edited maize plants were generated with a Cas nuclease, a Zm1d31709_Pro-242 gRNA comprising an RNA encoded by SEQ ID NO: 6, and a triplicated ZmOCS enhancer element donor DNA (SEQ ID NO: 18).

Figure 5:

FIG. 5 shows a "T Zero" (T0) ZM202 genetically edited maize plants comprising a transcription enhancer inserted in the Zm1d31709 gene promoter, a "T Zero" (T0) ZM203 genetically edited maize plants comprising a transcription enhancer inserted in the Zm1d44812 gene promoter, and a T0 ZM194 control plant lacking any transcription enhancer insertion. The T0 ZM202 genetically edited maize plants were generated with a Cas nuclease, a ZM1d31709_Pro-242 gRNA comprising an RNA encoded by SEQ ID NO: 6, and a triplicated ZmOCS enhancer element donor DNA (SEQ ID NO: 16). The T0 ZM203 genetically edited maize plants were generated with a Cas nuclease, a Zm1d44812_Pro-259 gRNA comprising an RNA encoded by SEQ ID NO: 15, and a triplicated ZmOCS enhancer element donor DNA (SEQ ID NO: 18).

Figure 6:

FIG. 6 shows two "T Zero" (T0) ZM185 genetically edited maize plants comprising a transcription enhancer inserted in the Zm1d31709 gene promoter, two "T Zero" (T0) ZM186 genetically edited maize plant comprising a transcription enhancer inserted in the Zm1d31709 gene promoter, and T0 ZM184 and Zm182 control plants lacking any transcription enhancer insertion. The T0 ZM185 and ZM186 genetically edited maize plants were generated with a Cas nuclease, a ZM1D31709_Pro-109 gRNA comprising an RNA encoded by SEQ ID NO: 4, and a triplicated ZmOCS enhancer element donor DNA (SEQ ID NO: 18).

Figure 7:
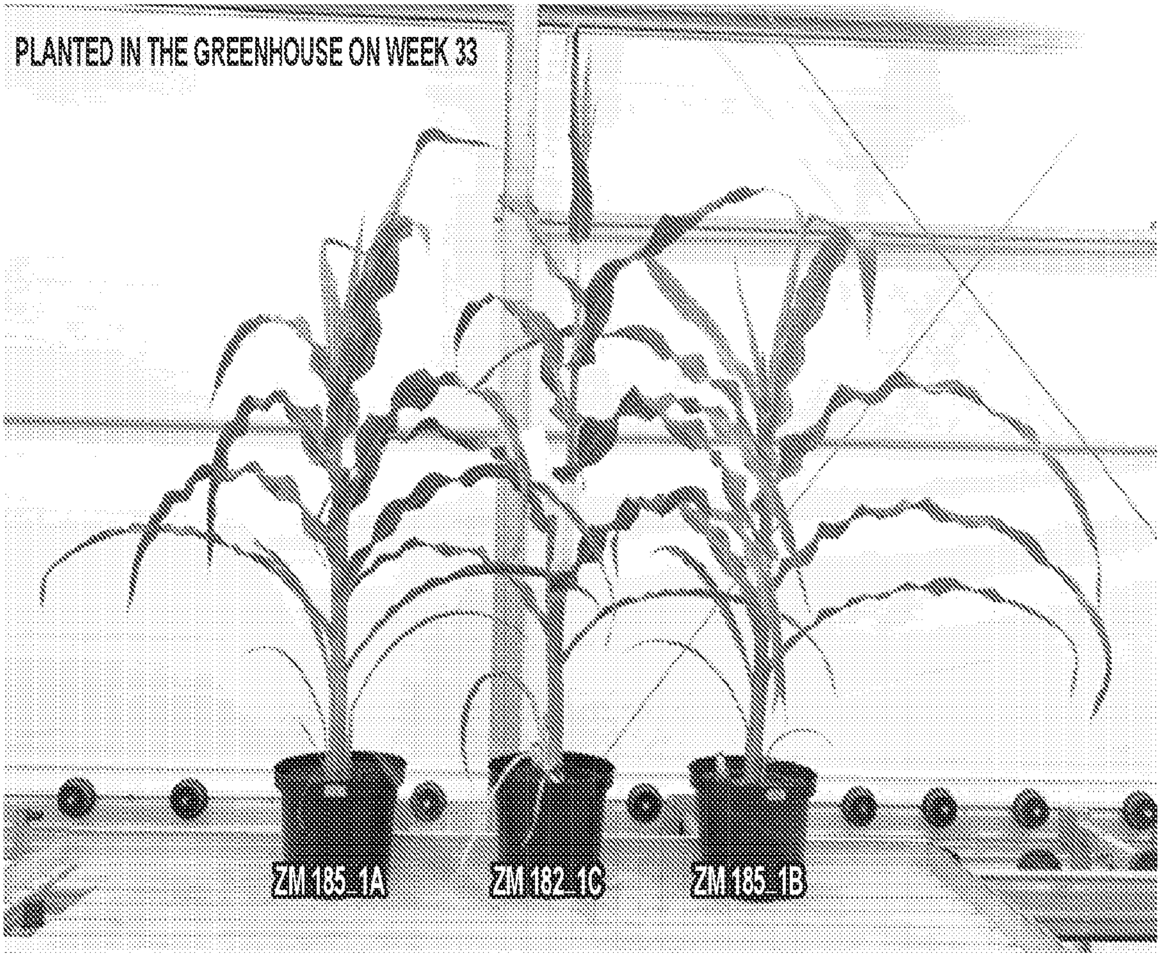

FIG. 7 shows two "T Zero" (T0) ZM185 genetically edited maize plants comprising a transcription enhancer inserted in the Zm1d31709 gene promoter and a TO Zm182 control plant lacking any transcription enhancer insertion. The T0 ZM185 genetically edited maize plants were generated with a Cas nuclease, a ZM1d31709 Pro-109 gRNA comprising an RNA encoded by SEQ ID NO: 4, and a triplicated ZmOCS enhancer element donor DNA (SEQ ID NO: 18).

Figure 8:

FIG. 8 shows five "T Zero" (T0) ZM187 genetically edited maize plants comprising a transcription enhancer inserted in the Zm1d44812 gene promoter and a T0 ZM190 control plant lacking the transcription enhancer insertion. The T0 ZM187 genetically edited maize plants were generated with a Cas nuclease, a Zm1d44812_Pro-75 gRNA comprising an RNA encoded by SEQ ID NO: 10, and a triplicated ZmOCS enhancer element donor DNA (SEQ ID NO: 18).

Figure 9:
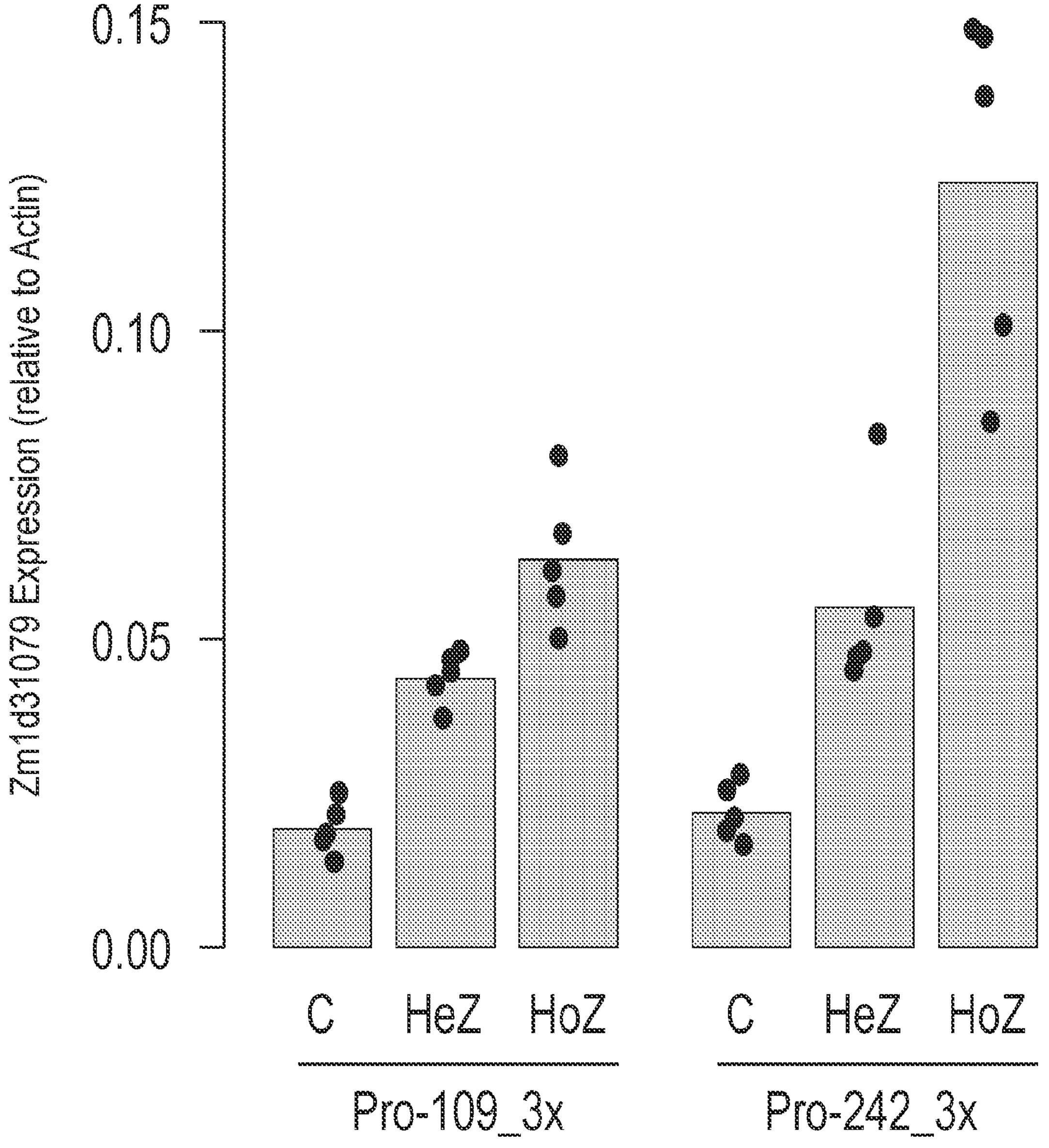

FIG. 9 shows expression of Zm1d31079 (SEQ ID NO:1) relative to a ZmAct1 (actin) control in young shoot apices in two populations segregating an enhancer insertion allele, comparing plants that do not contain an enhancer allele (C) to siblings that are heterozygous (HeZ) or homozygous (HoZ) for the triplicated ZmOCS enhancer allele at the indicated position (−109 or −242 relative to the TSS). Each data point represents the average of two technical replicates for one individual plant.

Figure 10:
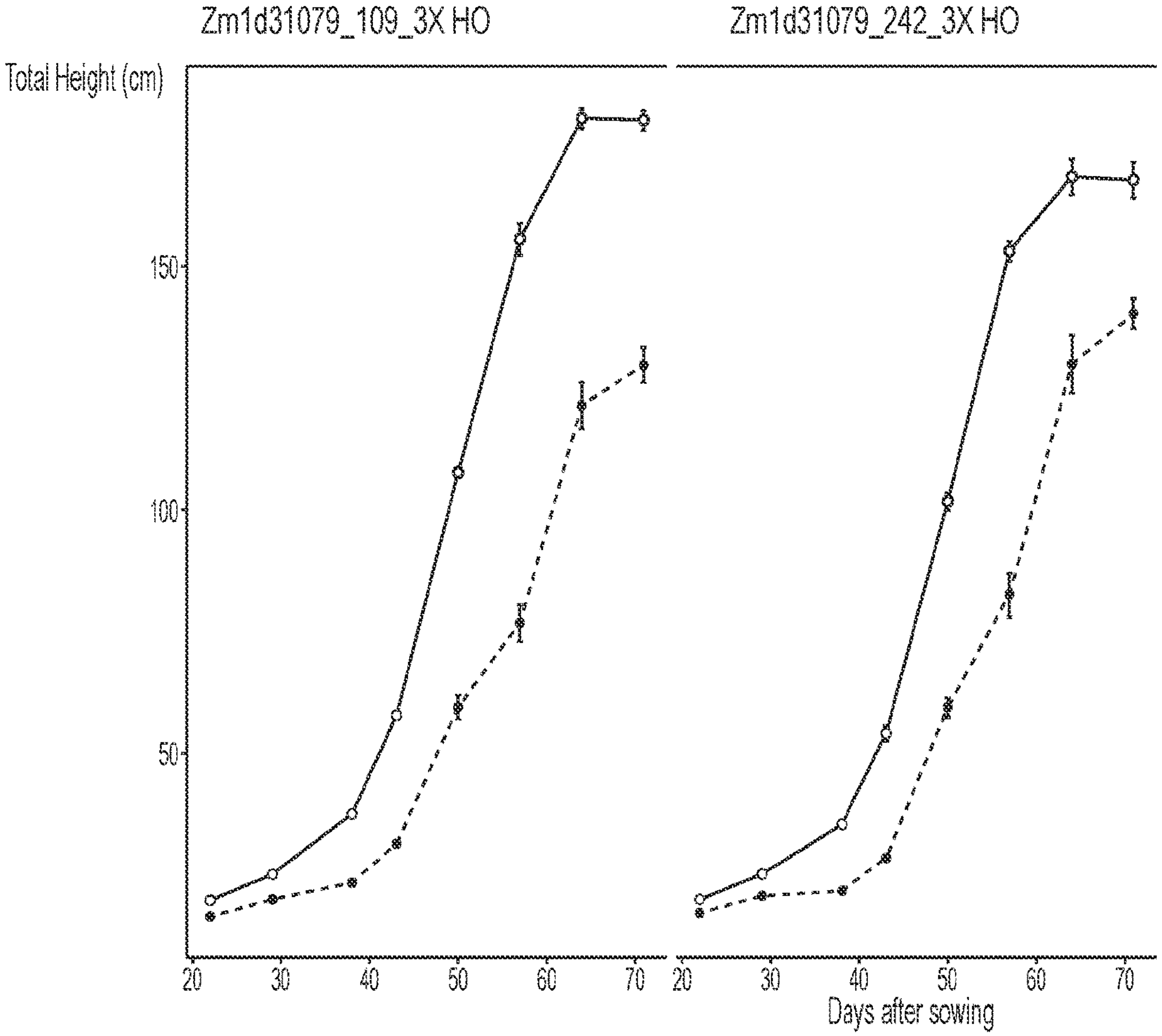

FIG. 10 shows plant height over time for segregating control plants to plants homozygous for the triplicated ZmOCS enhancer element inserted at the indicated position in the Zm1d31079 (SEQ ID NO:1) promoter. Average height±standard error is shown, with N=5-8 per group; triplicated ZmOCS enhancer element insertion homozygotes are in black (lower curve) and segregating controls which lack the enhancer insertion are in grey (upper curve).

DETAILED DESCRIPTION

The phrase "allelic variant" as used herein refers to a polynucleotide or polypeptide sequence variant that occurs in a particular gene at particular locus in a different strain, variety, or isolate of a given organism.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "biological sample" refers to either intact or non-intact (e.g., milled maize seed or maize plant tissue, chopped maize plant tissue, lyophilized tissue) maize plant tissue. It may also be an extract comprising intact or non-intact seed or maize plant tissue. The biological sample can comprise flour, meal, syrup, oil, starch, and cereals manufactured in whole or in part to contain maize plant products or by-products. In certain embodiments, the biological sample is "non-regenerable" (i.e., incapable of being regenerated into a maize plant or maize plant part).

As used herein, the terms "correspond," "corresponding," and the like, when used in the context of an nucleotide position, mutation, and/or substitution in any given polynucleotide (e.g., an allelic variant of SEQ ID NO: 1 or SEQ ID NO: 8) with respect to the reference polynucleotide sequence (e.g., SEQ ID NO: 1 or SEQ ID NO: 8) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe).

As used herein, the phrases "endogenous promoter," "endogenous gene," "endogenous plant transcription unit" and the like refer to the native form of a promoter, gene, or plant transcription unit in its natural location in the organism or in the genome of an organism.

As used herein, the term "exemplary" refers to an example, an instance, or an illustration, and does not indicate a preferred embodiment unless otherwise stated.

The term "heterologous" as used herein with regards to a DNA molecule, nucleotides, or polynucleotides inserted into a plant genome refer to any DNA molecule, nucleotide, or polynucleotide that is synthetic or that has been removed from its native location and that has been inserted into a new genomic location.

As used herein, the terms "include," "includes," and "including" are to be construed as at least having the features to which they refer while not excluding any additional unspecified features.

As used herein, the phrase "operably linked" refers to a juxtaposition wherein the components so described are in a relationship permitting them to function in their intended manner. For instance, a promoter is operably linked to a coding sequence if the promoter affects its transcription or expression. In another non-limiting example, an "expression enhancing element" (e.g., a transcription enhancer element) is operably linked to a promoter if the expression increasing element increases activity of the promoter (e.g., as measured by promoter-driven accumulation of a transcript or protein encoded by the transcript). In certain embodiments provided herein, a heterologous "expression enhancing element" (e.g., a transcription enhancer element) is operably linked to an endogenous plant promoter (e.g., a maize Zm1d31079 or Zm1d44812 gene promoter associated with the endogenous maize gene) which is located in a plant chromosome.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, flowers, or stalks. In contrast, some plant cells are not capable of being regenerated to produce plants and are referred to herein as "non-regenerable" plant cells.

As used herein, the terms "unmodified Zm1d31079 gene" and "Zm1d31079 protein" respectively refer to either the gene of SEQ ID NO: 1 and allelic variants thereof or the protein of SEQ ID NO: 2 and allelic variants thereof.

As used herein, the terms "unmodified Zm1d44812 gene" and "Zm1d44812 protein" respectively refer to either the gene of SEQ ID NO: 8 and allelic variants thereof or the protein of SEQ ID NO: 9 and allelic variants thereof.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Maize plants comprising a modified Zm1d31079 gene or a modified Zm1d44812 gene wherein a heterologous expression enhancing element is located in the modified gene and provides for increased expression of a Zm1d31079 or a Zm1d44812 gene product (e.g., a Zm1d31079 or a Zm1d44812 protein or RNA transcript encoding the protein) are disclosed. An endogenous and unmodified Zm1d31079 gene allele (SEQ ID NO: 1) is set forth in the "MaizeGDB" (maize genome database world wide web internet site "maizegdb.org") under accession number Zm00001d031079 and encodes the Zm1d31079 protein (SEQ ID NO: 2). An endogenous and unmodified Zm1d44812 gene (SEQ ID NO: 8) is set forth in the "MaizeGDB" (maize genome database world wide web internet site maizegdb.org) under accession number Zm00001d044812 and encodes the Zm1d44812 protein (SEQ ID NO: 9). The Zm1d44812 protein (SEQ ID NO: 9) has also been identified as the ZmPIN1a protein (Li, Z X et al. Plant Biotechnology Journal (2018) 16, pp. 86-99; doi: 10.1111/pbi.12751).

Allelic variants of an endogenous Zm1d31079 gene (SEQ ID NO: 1) and an endogenous Zm1d44812 gene (SEQ ID NO: 8) include sequence variants of both non-coding regions (e.g., promoter, 5' UTR, and 3' UTR set forth in SEQ ID NO: 1 and SEQ ID NO: 8) and coding regions (regions of the genes encoding the proteins of SEQ ID NO: 2 and SEQ ID NO: 9). Allelic variants of an endogenous Zm1d31079 gene include variants which encode Zm1d31079 proteins having at least 95%, 96%, 98%, 99%, or 99.5% sequence identity to SEQ ID NO: 2. Allelic variants of an endogenous Zm1d31079 gene also include variants having at least 95%, 96%, 98%, 99%, or 99.5% sequence identity to SEQ ID NO: 1. Allelic variants of an endogenous Zm1d44812 gene include variants which encode Zm1d44812 proteins having at least 95%, 96%, 98%, 99%, or 99.5% sequence identity to SEQ ID NO: 9. Allelic variants of an endogenous Zm1d44812 gene also include variants having at least 95%, 96%, 98%, 99%, or 99.5% sequence identity to SEQ ID NO: 8.

To obtain maize plants with reduced height and improved performance as both inbred parents and as a hybrids, it is desirable in certain embodiments to obtain an allelic series of maize plants comprising different modified Zm1d31079 genes or different modified Zm1d44812 genes. In the allelic series, distinct expression levels of the different modified Zm1d31079 gene or the different modified Zm1d44812 genes are obtained to produce plants with distinct reductions in height ranging from about 5% or 10% to about 15%, 20%, 30%, or 50% in comparison to control plants lacking the modified Zm1d31079 gene or the modified Zm1d44812 gene. In certain contexts, maize plants having a given Zm1d31079 gene or a modified Zm1d44812 gene results in lower reductions in height (e.g., from about 5% to about 15% in comparison to control plants) are selected from the allelic series in order to obtain plants having a desired height reduction. In certain contexts, maize plants having a given Zm1d31079 gene or a modified Zm1d44812 gene with results in lower reductions in height (e.g., from about 15% to about 20%, 30%, or 50% in comparison to control plants) are selected from the allelic series in order to obtain plants having a desired height reduction. In certain embodiments, maize plants having a given modified Zm1d31079 gene or a modified Zm1d44812 gene exhibit increases in expression of the Zm1d31079 gene or the Zm1d44812 gene in one or more maize tissues of about 10%, 15%, or 20% to about 30%, 40%, 50%, 60%, 70%, 80%, or 100% in comparison to a control maize plant lacking the modified Zm1d31079 gene or the modified Zm1d44812 gene are obtained in the allelic series. In certain embodiments, maize plants having a given modified Zm1d31079 gene or a modified Zm1d44812 gene exhibit in increases of expression of a Zm1d31079 gene product or a Zm1d44812 gene of about 1.2-fold or 1.5-fold to about 2-fold, 3-fold, or 5-fold in at least one maize tissue in the maize plant in comparison to a control maize plant lacking the modified Zm1d31079 gene or the modified Zm1d44812 gene. In certain embodiments, the desired height reduction and/or expression level can be selected based on performance characteristics (e.g., inbred and/or hybrid seed yield) for particular germplasms and/or for use in certain target geographies.

In certain embodiments, an allelic series of different modified Zm1d31079 genes or different modified Zm1d44812 genes can be obtained by insertion or formation of a transcription enhancer in the unmodified Zm1d31079 gene or unmodified Zm1d44812 gene such that the transcription enhancer is operably linked to the promoter of the gene but placed at different positions relative to the transcriptional start site (TSS). In certain embodiments, the allelic series can be obtained by locating the transcription enhancer at different positions from about 10, 20, 30, 40, 100, or 150 base pairs (bp) to about 200, 240, 300, 350, 400, 500, or 1000 bp 5' of the transcriptional start site (TSS) of the Zm1d31079 or Zm1d44812 gene. In certain embodiments, operable linkage to the endogenous promoter is achieved by insertion or formation of an enhancer in one or more of an endogenous promoter, 5' untranslated region (5'UTR), intron, and/or 3' untranslated region of an endogenous Zm1d31079 gene or endogenous Zm1d44812 gene located at its native chromosomal location (e.g., by CRISPR, TALEN, or artificial Zinc Finger mediated gene editing). Transcriptional enhancer elements that can be inserted or formed in the Zm1d31079 gene or Zm1d44812 gene promoter, 5' UTR, intron, or 3' UTR can comprise one or more DNA molecules set forth in SEQ ID NO:16, SEQ ID NO: 17, SEQ ID NO: 19-SEQ ID NO: 124, and/or SEQ ID NO: 125. In certain embodiments, two distinct enhancers independently selected from SEQ ID NO: 16, SEQ ID NO: 17, SEQ ID NO: 19-SEQ ID NO: 124, and/or SEQ ID NO: 125 are inserted or formed in the gene promoter, 5' UTR, intron, or 3' UTR. In certain embodiments, a distinct enhancer independently selected from SEQ ID NO:16, SEQ ID NO: 17, SEQ ID NO: 19-SEQ ID NO: 124, and/or SEQ ID NO: 125 are inserted or formed in the Zm1d31079 gene or Zm1d44812 gene promoter, 5' UTR, intron, or 3' UTR. In certain embodiments, members of a modified Zm1d31079 gene allelic series can comprise insertions of a transcription enhancer (e.g., one or more DNA molecules set forth in SEQ ID NO: 16, SEQ ID NO: 17, SEQ ID NO: 19-SEQ ID NO: 124, and/or SEQ ID NO: 125) at: (i) about 116 to about 96 base pairs or about 114, 112, 110, 108, 106, 104, 102, 100, or 98 base pairs 5' to the TSS of the Zm1d31079 gene; (ii) about 119 to about 99 base pairs or about 117, 115, 113, 111, or 109 base pairs 5' to the TSS of the Zm1d31079 gene; (iii) about 170 or 164 to about 150 base pairs or about 168, 166, 164, 162, 160, 158, 156, 154, or 152 base pairs 5' to the TSS of the Zm1d31079 gene; (iv) about 252 to about 242 base pairs or about 250, 248, 246, 244, 242, 240, 238 base pairs 5' to the TSS of the Zm1d31079 gene; (v) about 261 to about 241 base pairs or about 259, 257, 256, 253, 251, 249, 247, 245, or 243 base pairs 5' to the TSS of the Zm1d31079 gene; (v) in a double stranded break introduced in the Zm1d31079 promoter with a Cas9 nuclease and a guide RNA encoded by SEQ ID NO: 4, 5, or 6; or (vi) in a double stranded break introduced in the Zm1d31079 promoter with a Cas12 nuclease and a guide RNA encoded by SEQ ID NO: 3 or 7. In certain embodiments, insertions of the transcription enhancer at any of the aforementioned positions in the Zm1d31079 promoter is accompanied by the deletion of 1, 2, 3, 4, 5, 6, 7, 8, 9, 10, or more base pairs of DNA in the Zm1d31079 promoter either 5' and/or 3' to the transcription enhancer insertion in the corresponding DNA of SEQ ID NO: 1 or an allelic variant thereof. In certain embodiments, members of a modified Zm1d44812 gene allelic series can comprise insertions of a transcription enhancer (e.g., one or more DNA molecules set forth in SEQ ID NO:16, SEQ ID NO: 17, SEQ ID NO: 19-SEQ ID NO: 124, and/or SEQ ID NO: 125) at: (i) about 85 to about 65 base pairs or about 83, 81, 79, 77, 75, 73, 71, 69, or 67 base pairs 5' to the TSS of the Zm1d44812 gene; (ii) about 93 to about 73 base pairs or about 91, 89, 87, 85, 83, 81, 79, 77, or 75 base pairs 5' to the TSS of the Zm1d44812 gene; (iii) about 183 to about 163 base pairs or about 181, 179, 177, 175, 173, 171, 169, 167, or 165 base pairs 5' to the TSS of the Zm1d44812 gene; (iv) about 188 to about 168 base pairs or about 186, 184, 182, 180, 178, 176, 174, 172, or 170 base pairs 5' to the TSS of the Zm1d44812 gene; (v) about 269 to about 249 base pairs or about 267, 265, 263, 261, 259, 257, 255, 253, or 251 base pairs 5' to the TSS of the Zm1d44812 gene; (v) in a double stranded break introduced in the Zm1d44812 promoter with a Cas9 nuclease and a guide RNA encoded by SEQ ID NO: 10, 12, or 15; or (vi) in a double stranded break introduced in the Zm1d44812 promoter with a Cas12 nuclease and a guide RNA encoded by SEQ ID NO: 11, 13, or 14. In certain embodiments, insertions of the transcription enhancer at any of the aforementioned positions in the Zm1d44812 promoter is accompanied by the deletion of 1, 2, 3, 4, 5, 6, 7, 8, 9, 10, or more base pairs of DNA in the Zm1d44812 promoter either 5' and/or 3' to the transcription enhancer insertion in the corresponding DNA of SEQ ID NO: 1 or an allelic variant thereof. In certain embodiments, any of the aforementioned transcription enhancer insertions can be combined with an insertion of a heterologous translational enhancing element and/or a heterologous intron in the Zm1d31079 gene or Zm1d44812 gene. A list of useful transcriptional enhancer elements that can be used to obtain an allelic series of different modified Zm1d31079 genes or different modified Zm1d44812 genes is provided in Table 1.

TABLE 1

Transcriptional enhancer elements.

| Type of regulation | Name of element | Sequence[1] | SEQ ID NO: |
|---|---|---|---|
| up (constitutive) | 36 bp enhancer | GTAAGCGCTTACGTAAGCG CTTACGTAAGCGCTTAC | 16 |
| up (auxin responsive; constitutive) | 12-nt ocs orthologue (Zea mays) | GTAAGCGCTTAC | 17 |
| regulatory control by TF | ABFs binding site motif | CACGTGGC | 19 |
| regulatory control by TF | ABRE binding site motif | YACGTGGC | 20 |
| regulatory control by TF | ABRE-like binding site motif | BACGTGKM | 21 |
| regulatory control by TF | ACE promoter motif | GACACGTAGA | 22 |
| regulatory control by TF | AG binding site motif | TTDCCWWWWWWGGH | 23 |
| regulatory control by TF | AG binding site in AP3 | CCATTTTTAGT | 24 |
| regulatory control by TF | AG binding site in SUP | CCATTTTTGG | 25 |
| regulatory control by TF | AGLI binding site motif | NTTDCCWWWWNNGGWAA N | 26 |
| regulatory control by TF | AGL2 binding site motif | NNWNCCAWWWWTRGWW AN | 27 |
| regulatory control by TF | AGL3 binding site motif | TTWCYAWWWWTRGWAA | 28 |
| regulatory control by TF | AP1 binding site in AP3 | CCATTTTTAG | 29 |
| regulatory control by TF | ARF binding site motif | TGTCTC | 30 |
| regulatory control by TF | ATHB1 binding site motif | CAATWATTG | 31 |
| regulatory control by TF | ATHB2 binding site motif | CAATSATTG | 32 |
| regulatory control by TF | ATHB5 binding site motif | CAATNATTG | 33 |
| regulatory control by TF | ATHB6 binding site motif | CAATTATTA | 34 |
| regulatory control by TF | AtMYB2 binding site in RD22 | CTAACCA | 35 |
| regulatory control by TF | AtMYC2 binding site in RD22 | CACATG | 36 |
| regulatory control by TF | Box II promoter motif | GGTTAA | 37 |
| regulatory control by TF | CArG promoter motif | CCWWWWWWGG | 38 |

TABLE 1-continued

| Transcriptional enhancer elements. | | | |
|---|---|---|---|
| Type of regulation | Name of element | Sequence[1] | SEQ ID NO: |
| regulatory control by TF | CArG1 motif in AP3 | GTTTACATAAATGGAAAA | 39 |
| regulatory control by TF | CArG2 motif in AP3 | CTTACCTTTCATGGATTA | 40 |
| regulatory control by TF | CArG3 motif in AP3 | CTTTCCATTTTTAGTAAC | 41 |
| regulatory control by TF | CBF1 binding site in cor15a | TGGCCGAC | 42 |
| regulatory control by TF | CBF2 binding site motif | CCACGTGG | 43 |
| regulatory control by TF | CCA1 binding site motif | AAMAATCT | 44 |
| regulatory control by TF | CCA1 motif1 binding site in CAB1 | AAACAATCTA | 45 |
| regulatory control by TF | CCA1 motif2 binding site in CAB1 | AAAAAAAATCTATGA | 46 |
| regulatory control by TF | DPBF1&2 binding site motif | ACACNNG | 47 |
| regulatory control by TF | DRE promoter motif | TACCGACAT | 48 |
| regulatory control by TF | DRE-like promoter motif | DRCCGACNW | 49 |
| regulatory control by TF | E2F binding site motif | TTTCCCGC | 50 |
| regulatory control by TF | E2F-varient binding site motif | TCTCCCGCC | 51 |
| regulatory control by TF | EIL 1 binding site in ERF1 | TTCAAGGGGGCATGTATCT TGAA | 52 |
| regulatory control by TF | EIN3 binding site in ERF1 | GGATTCAAGGGGGCATGTA TCTTGAATCC | 53 |
| regulatory control by TF | ERE promoter motif | TAAGAGCCGCC | 54 |
| regulatory control by TF | ERF1 binding site in AtCHI-B | GCCGCC | 55 |
| regulatory control by TF | Evening Element promoter motif | AAAATATCT | 56 |
| regulatory control by TF | GATA promoter motif | WGATAR | 57 |
| regulatory control by TF | GBF1/2/3 binding site in ADH1 | CCACGTGG | 58 |
| regulatory control by TF | G-box promoter motif | CACGTG | 59 |
| regulatory control by TF | GCC-box promoter motif | GCCGCC | 60 |
| regulatory control by TF | GT promoter motif | TGTGTGGTTAATATG | 61 |
| regulatory control by TF | Hexamer promoter motif | CCGTCG | 62 |
| regulatory control by TF | HSEs binding site motif | AGAANNTTCT | 63 |

TABLE 1-continued

| Transcriptional enhancer elements. | | | |
|---|---|---|---|
| Type of regulation | Name of element | Sequence[1] | SEQ ID NO: |
| regulatory control by TF | Ibox promoter motif | GATAAG | 64 |
| regulatory control by TF | JASE1 motif in OPR1 | CGTCAATGAA | 65 |
| regulatory control by TF | JASE2 motif in OPR2 | CATACGTCGTCAA | 66 |
| regulatory control by TF | L1-box promoter motif | TAAATGYA | 67 |
| regulatory control by TF | LS5 promoter motif | ACGTCATAGA | 68 |
| regulatory control by TF | LS7 promoter motif | TCTACGTCAC | 69 |
| regulatory control by TF | LTRE promoter motif | ACCGACA | 70 |
| regulatory control by TF | MRE motif in CHS | TCTAACCTACCA | 71 |
| regulatory control by TF | MYB binding site promoter | MACCWAMC | 72 |
| regulatory control by TF | MYB1 binding site motif | MTCCWACC | 73 |
| regulatory control by TF | MYB2 binding site motif | TAACTSGTT | 74 |
| regulatory control by TF | MYB3 binding site motif | TAACTAAC | 75 |
| regulatory control by TF | MYB4 binding site motif | AMCWAMC | 76 |
| regulatory control by TF | Nonamer promoter motif | AGATCGACG | 77 |
| regulatory control by TF | OBF4,5 binding site in GST6 | ATCTTATGTCATTGATGAC GACCTCC | 78 |
| regulatory control by TF | OBP-1,4,5 binding site in GST6 | TACACTTTTGG | 79 |
| regulatory control by TF | OCS promoter motif | TGACGYAAGSRMTKACGY MM | 80 |
| regulatory control by TF | octamer promoter motif | CGCGGATC | 81 |
| regulatory control by TF | PI promoter motif | GTGATCAC | 82 |
| regulatory control by TF | PII promoter motif | TTGGTTTTGATCAAAACCA A | 83 |
| regulatory control by TF | PRHA binding site in PAL1 | TAATTGACTCAATTA | 84 |
| regulatory control by TF | RAV1-A binding site motif | CAACA | 85 |
| regulatory control by TF | RAV1-B binding site motif | CACCTG | 86 |
| regulatory control by TF | RY-repeat promoter motif | CATGCATG | 87 |
| regulatory control by TF | SBP-box promoter motif | TNCGTACAA | 88 |

TABLE 1-continued

Transcriptional enhancer elements.

| Type of regulation | Name of element | Sequence[1] | SEQ ID NO: |
|---|---|---|---|
| regulatory control by TF | T-box promoter motif | ACTTTG | 89 |
| regulatory control by TF | TEF-box promoter motif | AGGGGCATAATGGTAA | 90 |
| regulatory control by TF | TELO-box promoter motif | AAACCCTAA | 91 |
| regulatory control by TF | TGA1 binding site motif | TGACGTGG | 92 |
| regulatory control by TF | W-box promoter motif | TTGAC | 93 |
| regulatory control by TF | Z-box promoter motif | ATACGTGT | 94 |
| regulatory control by TF | AG binding site in SPL/NOZ | AAAACAGAATAGGAAA | 95 |
| regulatory control by TF | Bellringer/replumless/ pennywise binding site IN AG | AAATTAAA | 96 |
| regulatory control by TF | Bellringer/replumless/ pennywise binding site 2 in AG | AAATTAGT | 97 |
| regulatory control by TF | Bellringer/replumless/ pennywise binding site 3 in AG | ACTAATTT | 98 |
| regulatory control by TF | AGL15 binding site in AtGA2ox6 | CCAATTTAATGG | 99 |
| regulatory control by TF | ATB2/AtbZIP53/AtbZIP44/ GBF5 binding site in ProDH | ACTCAT | 100 |
| regulatory control by TF | LFY binding site in AP3 | CTTAAACCCTAGGGGTAAT | 101 |
| regulatory control by TF | SORLREP1 | TTWTACTAGT | 102 |
| regulatory control by TF | SORLREP2 | ATAAAACGT | 103 |
| regulatory control by TF | SORLREP3 | TGTATATAT | 104 |
| regulatory control by TF | SORLREP4 | CTCCTAATT | 105 |
| regulatory control by TF | SORLREP5 | TTGCATGACT | 106 |
| regulatory control by TF | SORLIP1 | AGCCAC | 107 |
| regulatory control by TF | SORLIP2 | GGGCC | 108 |
| regulatory control by TF | SORLIP3 | CTCAAGTGA | 109 |
| regulatory control by TF | SORLIP4 | GTATGATGG | 110 |
| regulatory control by TF | SORLIP5 | GAGTGAG | 111 |

TABLE 1-continued

Transcriptional enhancer elements.

| Type of regulation | Name of element | Sequence[1] | SEQ ID NO: |
|---|---|---|---|
| regulatory control by TF | ABFs binding site motif | CACGTGGC | 112 |
| up (auxin responsive) | 3xDR5 auxin-response element | CCGACAAAAGGCCGACAA AAGGCCGACAAAAGGT | 113 |
| up (auxin responsive) | 3xDR5 auxin-response element | ACCTTTTGTCGGCCTTTTGT CGGCCTTTTGTCGG | 114 |
| up (auxin responsive) | 6xDR5 auxin-responsive element | GCCGACAAAAGGCCGACA AAAGGCCGACAAAAGGCC GACAAAAGGCCGACAAAA GGCCGACAAAAGGT | 115 |
| up (auxin responsive) | 6xDR5 auxin-responsive element | ACCTTTTGTCGGCCTTTTGT CGGCCTTTTGTCGGCCTTTT GTCGGCCTTTTGTCGGCCTT TTGTCGGC | 116 |
| up (auxin responsive) | 9xDR5 auxin-responsive element | CCGACAAAAGGCCGACAA AAGGCCGACAAAAGGCCG ACAAAAGGCCGACAAAAG GCCGACAAAAGGCCGACA AAAGGCCGACAAAAGGCC GACAAAAGGT | 117 |
| up (auxin responsive) | 9xDR5 auxin-responsive element | ACCTTTTGTCGGCCTTTTGT CGGCCTTTTGTCGGCCTTTT GTCGGCCTTTTGTCGGCCTT TTGTCGGCCTTTTGTCGGCC TTTTGTCGGCCTTTTGTCGG | 118 |
| up (auxin responsive; constitutive) | ocs enhancer (*Agrobacterium* sp.) | ACGTAAGCGCTTACGT | 119 |
| up (nitrogen responsive) | AtNRE | AAGAGATGAGCTCTTGAGC AATGTAAAGGGTCAAGTTG TTTCT | 120 |
| up (nitrogen responsive) | AtNRE | AGAAACAACTTGACCCTTT ACATTGCTCAAGAGCTCAT CTCTT | 121 |
| up (auxin responsive) | 3xDR5 auxin-response element; complementary strand of a hybrid | ACCTTTTGTCGGCCTTTTGT CGGCCTTTTGTCGG | 122 |
| up (auxin responsive) | 3xDR5 auxin-response element; sticky-ended | TCGGTCCGACAAAAGGCCG ACAAAAGGCGGACAAAAG G | 123 |
| up (auxin responsive) | 3xDR5 auxin-response element; sticky-ended | ACCGACCTTTTGTCGGCCTT TTGTCGGCCTTTTGTCGG | 124 |
| up (Pi starvation response) | P1BS | GNATATNC | 125 |

[1] Y = T or C; W = A or T; S = C or G; M = A or C; N = A, G, C, or T; K = G or T; R = A or G; K = G or T; D = A, G, or T; B = C, G, or T; H = A, C, or T

The transcriptional enhancer element of SEQ ID NO: 16 comprises 3 copies of a 12-nucleotide core element nucleotide sequence of SEQ ID NO: 17. The 12 nucleotide core element nucleotide sequence of SEQ ID NO: 17 is present at several locations in the maize genome. For example, it can be found at several chromosomal locations of the maize variety B73. According to the B73v4 version of the genomic sequences (available on the https world wide web internet site maizegdb.org/genome/assembly/Zm-B73-REFERENCE-GRAMENE-4.0 and hereinafter referred to as "B73v4 maize genome"), SEQ ID NO: 17 can be found on Chr3 coordinates 1,063,395..1,063,406 (intron of Zm00001d039287), on Chr3 coordinates 12,253,969..12,253,980 (immediately downstream of Zm00001d039695), on Chr3 coordinates 12,265,615..12,265,626 (intron of Zm00001d039695), on Chr3 coordinates 12,277,428..12,277,439 (intron of Zm00001d039695), on Chr3 coordinates 147,698,750..147,698,761 (not within 2 kb of an annotated gene model), on Chr6, coordinates 107,132,183..107,132,194 (about 2 kb downstream of Zm00001d036949), on Chr10, coordinates 53,761,662..53,761,673 (not within 2 kb of an annotated gene model).

In certain embodiments, a modified Zm1d31079 gene or modified Zm1d44812 gene with increased expression that provides for reduced plant height is obtained by inserting a heterologous intron in the 5' UTR and/or within the coding region of a Zm1d31079 gene or the Zm1d44812 gene. Materials and methods for intron mediated enhancement (IME) of plant gene expression described previously (Laxa, M. Front. Plant Sci., 6 Jan. 2017 doi.org/10.3389/fpls.2016.01977; Rose, A. B. Plant J. 17 Nov. 2004 doi.org/10.1111/j.1365-313X.2004.02247.x; Parra, G. et al. Nucleic Acids Research, Volume 39, Issue 13, 1 Jul. 2011, 5328-5337, doi.org/10.1093/nar/gkr043) can be adapted for use in enhancing expression of Zm1d31079 gene or Zm1d44812 gene. Heterologous introns that can be used to increase expression of plant genes include an Actin, Hsp70, PEPC, UBQ (e.g., UBQ1, UBQ10), EF-1α, EF-1β, Histone H3, ATPK1, RHD3, or MHX intron (e.g., a rice or maize Actin, Hsp70, PEPC, UBQ1, UBQ10, EF-1α, EF-1β, Histone H3, ATPK1, RHD3, or MHX intron). In certain embodiments, the intron is inserted within or at about 500, 200, 100, 50, 30, or 20 base pairs of the transcription start site (TSS). In certain embodiments, the intron is inserted in the 5' UTR and/or in the coding region within at about 500, 200, 100, 50, 30, or 20 base pairs of the transcription start site (TSS) of a Zm1d31079 gene or the Zm1d44812 gene. In certain embodiments, the intron is inserted in the 5' UTR and/or in the coding region within at about 20 to about 100 or 200 base pairs of the transcription start site (TSS) of a Zm1d31079 gene or the Zm1d44812 gene.

In certain embodiments, a modified Zm1d31079 gene or modified Zm1d44812 gene with increased expression that provides for reduced plant height is obtained by inserting a heterologous translational enhancer in the 5' UTR and/or within the coding region of the Zm1d31079 gene or the Zm1d44812 gene. Translational enhancers can comprise 5' UTRs and/or 5' UTR and one or more codons of a coding region. Translational enhancers include 5' UTRs of various rice genes that can enhance translation of linked heterologous reporter genes (e.g., a 5' UTR of a rice Adh gene (Sugio et al. J. Biosci. Bioengin. 105(3), 300-302 (2008) doi.org/10.1263/jbb.105.300; glutathione transferase U50, glutathione peroxidase 1, 20S proteasome alpha1 subunit, pathogenesis-related protein 4b, glycine-rich cell-wall structural protein 1, or UspA domain containing protein; Yamasaki et al. Plant Biotechnology 35, 365-373 (2018) DOI: 10.5511/plantbiotechnology.18.0903a). In certain embodiments, the translational enhancer is encoded by a DNA molecule comprising the DNA sequence of any aforementioned 5'UTR and all or part of the 5'UTR is substituted for all or part of the Zm1d31079 5' UTR or the Zm1d44812 5' UTR in the modified Zm1d31079 or the modified Zm1d44812 gene.

Expression of a Zm1d31079 or Zm1d44812 encoding transgene can also be increased by in vitro insertion or formation of the in the transgene such that it is operably linked to the promoter that is operably linked to transgene and then introducing the transgene into the maize plant genome (e.g., by *Agrobacterium*-mediated transformation or biolistics). In certain embodiments, such transgenes can comprise a modified promoter that comprises any of the aforementioned modified Zm1d31079 or Zm1d44812 with the insertions and/or substitutions of the aforementioned transcription enhancers. In certain embodiments, such transgenes can comprise a whole or partial substitution of a Zm1d31079 or Zm1d44812 promoter, 5' UTR, and/or intron with a heterologous promoter, 5' UTR, and/or intron.

Expression of a modified Zm1d31079 gene or the modified Zm1d44812 gene can be increased in comparison to a control maize plant comprising the unmodified Zm1d31079 gene or the unmodified Zm1d44812 gene. Such increases in expression can be measured by a variety of methods. In certain embodiments, a reduced plant height trait conferred by increased expression of a modified Zm1d31079 gene or the modified Zm1d44812 gene is measured in maize plants comprising the expression increasing element and compared to control maize plants comprising the unmodified Zm1d31079 gene or the unmodified Zm1d44812 gene. Reduction in height traits can be assessed by comparing any measure of the reduced height trait itself (e.g., total height, internode length, etc.) or a proxy for the trait (e.g., yield of seed and/or other biomass in kg/hectare) in maize plants comprising the modified Zm1d31079 gene or the modified Zm1d44812 gene can be increased in comparison to a control maize plant comprising the unmodified Zm1d31079 gene or the unmodified Zm1d44812 gene. In certain embodiments, increased expression of the encoded transcript itself is directly measured by determining amounts of the Zm1d31079 gene or the Zm1d44812 gene-encoding transcript (e.g., an mRNA or non-coding RNA) in maize plants comprising the modified Zm1d31079 gene or the modified Zm1d44812 gene and compared to amounts of the transcript-encoding polynucleotide in control maize plants comprising the unmodified Zm1d31079 gene or the unmodified Zm1d44812 gene. Amounts of the Zm1d31079 gene or the Zm1d44812 gene-encoding transcript can be determined by a variety of techniques including PCR (e.g., quantitative reverse-transcriptase PCR; qRT-PCR), hybridization, CRISPR-, and/or sequencing-based techniques (Khodakov et al., doi.org/10.1016/j.addr.2016.04.005; Gootenberg, et al. doi: 10.1126/science.aaq0179). In certain embodiments, expression of a Zm1d31079 gene or the Zm1d44812 gene-encoding polynucleotide can also be determined by measuring amounts of a Zm1d31079 or the Zm1d44812 protein encoded by the transcript in maize plants comprising the transcription enhancer and compared to amounts of the Zm1d31079 or the Zm1d44812 protein in control maize plants comprising the unmodified Zm1d31079 gene or the unmodified Zm1d44812 gene. Amounts of the Zm1d31079 or the Zm1d44812 protein can be determined by a variety of techniques including immunoassays for the protein, and mass spectroscopy-based techniques (Chen et al. doi: 10.1186/s12967-015-0537-6; Bruce et al. doi: 10.1002/0471250953.bi1321s41). The magnitude of the increase in transcript production may depend on the baseline expression level of the unmodified endogenous Zm1d31079 or the Zm1d44812 transcript-encoding polynucleotide in the respective cells or tissues. By way of a non-limiting example, the magnitude of the increase in expression of an endogenous Zm1d31079 or the Zm1d44812 gene modified by insertion or formation of SEQ ID NO: 16 in an endogenous Zm1d31079 or the Zm1d44812 promoter over baseline expression levels of the unmodified endogenous Zm1d31079 or the Zm1d44812 gene will be greatest where baseline Zm1d31079 or the Zm1d44812 expression levels are low. In certain embodiments, expression of the endogenous Zm1d31079 or the Zm1d44812 gene modified by insertion of a heterologous expression enhancer (e.g., the transcription enhancer of SEQ ID NO: 16) can be increased by at least 1.2-, 1.5-, 2-, 3-, 4-, or 5-fold over baseline expression levels of the unmodified endogenous Zm1d31079 or the Zm1d44812 gene. In certain embodiments, expression of the endogenous Zm1d31079 or the Zm1d44812 gene modified by insertion or formation of the heterologous expression enhancer (e.g., the transcription enhancer of SEQ ID NO: 16) can be increased by at least about 1.2- or 1.5-fold to about 2-, 3-, 4-, 5-, 6-fold or more over baseline expression levels of the unmodified endogenous Zm1d31079 or the Zm1d44812 gene in unmodified control plants.

In certain embodiments, it will be desirable to use genome editing molecules to introduce or form a heterologous expression enhancing element (e.g., a heterologous transcription enhancer, a heterologous translational enhancing element, and/or a heterologous intron) in an endogenous Zm1d31079 or the Zm1d44812 gene. Gene editing molecules of use in methods provided herein include molecules capable of introducing a double-strand break ("DSB") or single-strand break ("SSB") at a specific site or sequence in a double-stranded DNA, such as in genomic DNA or in a target gene located within the genomic DNA as well as accompanying guide RNA or donor or other DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for use with an RNA-guided nuclease, or a DNA encoding a gRNA for use with an RNA-guided nuclease; (d) donor DNA template polynucleotides suitable for insertion at a break in genomic DNA by homology-directed repair (HDR) or microhomology-mediated end joining (MMEJ); and (e) other DNA templates (e.g., dsDNA, ssDNA, or combinations thereof) suitable for insertion at a break in genomic DNA (e.g., by non-homologous end joining (NHEJ).

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Plant RNA promoters for expressing CRISPR guide RNA and plant codon optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). In certain embodiments, an RNA-guided endonuclease that leaves a blunt end following cleavage of the target site is used. Blunt-end cutting RNA-guided endonucleases include Cas9, Cas12c, Cas12i, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e. Target Cas nuclease cleavage sites in both the promoters of the endogenous Zm1d31079 or the Zm1d44812 gene are set forth respectively in SEQ ID NO: 1 and SEQ ID NO: 8 as depicted in FIGS. 1 and 2. All of the patent publications referenced in this paragraph are incorporated herein by reference in their entirety.

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., maize plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, maize plants or maize plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017) Genes vol. 8,12: 399; Ramirez et al. Nucleic Acids Res. (2012); 40(12): 5560-5568; Liu et al. (2013) Nature Communications, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc “fingers” each recognizing a specific triplet of DNA. A number of strategies can be used to design the binding specificity of the zinc finger binding domain. One approach, termed “modular assembly”, relies on the functional autonomy of individual zinc fingers with DNA. In this approach, a given sequence is targeted by identifying zinc fingers for each component triplet in the sequence and linking them into a multi-finger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as Fokl. This endonuclease must dimerize to cleave DNA. Thus, cleavage by Fokl as part of a ZFN requires two adjacent and independent binding events, which must occur in both the correct orientation and with appropriate spacing to permit dimer formation. The requirement for two DNA binding events enables more specific targeting of long and potentially unique recognition sites. Fokl variants with enhanced activities have been described and can be adapted for use in the methods described herein; see, e.g., Guo et al. (2010) J. Mol. Biol., 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fokl, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) Genes vol. 8,12: 399). TALE nickases have also been described and can be adapted for use in methods described herein (Wu et al.; Biochem Biophys Res Commun. (2014); 446(1):261-6; Luo et al; Scientific Reports 6, Article number: 20657 (2016)).

In certain embodiments where heterologous expression enhancing element (e.g., a heterologous transcription enhancer, a heterologous translational enhancing element, and/or a heterologous intron) is inserted into the genome at a site of a double stranded break in the endogenous Zm1d31079 or the Zm1d44812 gene introduced by one or more nucleases or nickases (e.g., a CRISPR/guide RNA complex with site-specific endonuclease or nickase, an aZF nuclease or nickase, and/or a TALE nuclease or nickase), the donor DNA template or other DNA template comprises the heterologous expression enhancing element (e.g., a heterologous transcription enhancer, a heterologous translational enhancing element, and/or a heterologous intron). In certain embodiments where the heterologous expression enhancing element is formed in the genome at a site of a double stranded break in the maize plant genome introduced by a nuclease, the donor DNA template or other DNA template can comprise less than the complete set of nucleotides or base pairs of the transcription enhancer (e.g., less than the entire 36 nucleotides or base pairs of SEQ ID NO: 16 sequence) and genomic DNA at the site of integration can contribute the nucleotides or base pairs of the transcription enhancer that are absent from the donor DNA template or other DNA template. In certain embodiments where SEQ ID NO: 16 is formed in the genomic DNA, the donor DNA template or other DNA template can comprise up to 35 contiguous nucleotides or base pairs of SEQ ID NO:16, the genomic DNA at the site of integration can contribute 1 or more nucleotides or base pairs of the SEQ ID NO:16 sequence which are lacking from the donor DNA template or other DNA template, and the complete 36 base pair sequence of SEQ ID NO:16 is formed at the site of integration in the genome. Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In one embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 1, 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand of the targeted integration site (in the case of a perfectly base-paired double-stranded polynucleotide molecule). Such donor DNA templates can be integrated in genomic DNA containing blunt and/or staggered double stranded DNA breaks by homology-directed repair (HDR) or microhomology-mediated end joining (MMEJ). In certain embodiments, a donor DNA template homology arm can be about 20, 50, 100, 200, 400, or 600 to about 800, or 1000 base pairs in length. In certain embodiments, integration of the donor DNA templates by HDR can be facilitated by use of an exonuclease (e.g., bacteriophage lambda exonuclease), a single-stranded DNA annealing protein (SSAP; e.g., bacteriophage lambda beta SSAP protein), and a single-stranded DNA binding protein (SSB; e.g., an *E. coli* SSB) essentially as set forth in US Patent Application Publication 20200407754, which is incorporated herein by reference in its entirety. In certain embodiments, a donor DNA template molecule can be delivered to a maize plant cell in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. In other embodiments, DNA templates suitable for NHEJ insertion will lack homology arms that are partially or completely homologous to genomic DNA (gDNA) sequences flanking a target site-specific endonuclease cleavage site in the gDNA. In certain embodiments, the DNA template comprising all of an expression enhancing element (e.g., dsDNA, ssDNA, or combinations thereof) can be inserted at a double-stranded break in gDNA by non-homologous end joining (NHEJ). In certain embodiments, the DNA template (e.g., dsDNA, ssDNA, or combinations thereof) comprising less than the complete set of nucleotides of the expression enhancing element (e.g., a transcription enhancer less than 36 nucleotides or base pairs of SEQ ID NO:16 sequence) can be inserted at a double-stranded break in gDNA by non-homologous end joining (NHEJ), gDNA at the site of insertion can contribute the nucleotides or base pairs of the expression enhancing element (e.g., SEQ ID NO:16) that are absent from the DNA template, and the expression enhancing element (e.g., SEQ ID NO:16) can be formed at the site of the double-stranded break in the gDNA.

In some embodiments, the expression enhancing element (e.g., a heterologous transcription enhancer, a heterologous translational enhancing element, and/or a heterologous intron) replaces or largely replaces a corresponding sequence in a gene, such as in a promoter, a 5' UTR, or an intron. Accordingly, a replacement rather than an insertion leaves the positioning of other elements unchanged. A replacement target site may be chosen by similarity to the expression enhancing element or a portion thereof. A replacement template could be used in an HDR process, and/or DNA base editing and/or genome editing could be used to produce the desired replacement region that corresponds to the expression enhancing element or a portion thereof. Base editors include for example, a site-specific base edit mediated by a C*G to T•A or an A•T to G*C base editing deaminase enzymes (Gaudelli et al., Programmable base editing of A•T to G*C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. Catalytically dead dCas9 fused to a cytidine deaminase or an adenine deaminase protein becomes a specific base editor that can alter DNA bases without inducing a DNA break. Base editors convert C→T (or G→A on the opposite strand) or an adenine base editor that would convert adenine to inosine, resulting in an A→G change within an editing window specified by the gRNA.

Various treatments can be used for delivery of gene editing molecules and/or other molecules to a plant cell. In certain embodiments, one or more treatments is employed to deliver the gene editing or other molecules (e.g., comprising a polynucleotide, polypeptide, or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP (ribonucleoprotein)-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., Azobacter sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) Nature, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

Commodity plant products obtained from maize plants or maize plant parts comprising at least one modified Zm1d31079 gene or the modified Zm1d44812 gene as well as methods for making such products are provided. In certain embodiments, the commodity products are processed products are made from the maize plant or its seeds, including: (a) maize seed meal (defatted or non-defatted); (b) extracted maize proteins, oils, sugars, syrups, and starches; (c) soy fermentation products; (d) maize based animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral); (e) a pharmaceutical; (f) raw or processed biomass (e.g., cellulosic and/or lignocellulosic material; silage); and (g) various industrial products.

Also provided herein are methods for detecting a DNA fragment comprising a modified Zm1d31079 gene or the modified Zm1d44812 gene comprising a detectable amount of a DNA molecule comprising a heterologous transcription enhancer, a heterologous intron, and/or heterologous translational enhancing element located in a DNA fragment of a modified Zm1d31079 gene or in a DNA fragment of a modified Zm1d44812 gene in any of the aforementioned biological samples and commodity products. Non-limiting and illustrative examples of such DNA fragments include those wherein the SEQ ID NO: 16 enhancer is inserted. Detection of the DNA molecules comprising insertions and/or substitutions of the enhancer in the transcriptional regulatory region can be achieved by any combination of nucleic acid amplification (e.g., PCR amplification), hybridization, sequencing, and/or mass-spectrometry based techniques. Methods set forth for detecting foreign nucleic acids in transgenic loci set forth in US 20190136331 and U.S. Pat. No. 9,738,904, both incorporated herein by reference in their entireties, can be adapted for use in detection of the nucleic acids provided herein. In certain embodiments, such detection is achieved by amplification and/or hybridization-based detection methods using a method (e.g., selective amplification primers) and/or probe (e.g., capable of selective hybridization or generation of a specific primer extension product) which specifically recognizes the target DNA molecule (e.g., a heterologous transcription enhancer, a heterologous intron, and/or heterologous translational enhancing element located in a DNA fragment of a modified Zm1d31079 gene or in a DNA fragment of a modified Zm1d44812 gene) but does not recognize DNA from an unmodified Zm1d31079 gene or Zm1d44812 gene. In certain embodiments, the hybridization probes (e.g., polynucleotides comprising at least about 18 to 30 base pairs which span the junction of a, respectively) can comprise detectable labels (e.g., fluorescent, radioactive, epitope, and chemiluminescent labels). In certain embodiments, a single nucleotide polymorphism detection assay can be adapted for detection of the target DNA molecule (e.g., a heterologous transcription enhancer, a heterologous intron, and/or heterologous translational enhancing element located in a DNA fragment of a modified Zm1d31079 gene or in a DNA fragment of a modified Zm1d44812 gene).

Inbred and hybrid maize plants and seeds comprising a modified Zm1d31079 gene or the modified Zm1d44812 gene are provided herein along with methods for making and using such hybrid and inbred seed. Methods for inbred seed production include selfing inbred maize plants and restricting cross-pollination by any maize plants other than the inbred maize plant. Methods for production of such hybrid seed can comprise crossing elite crop maize plant lines where at least one of the pollen donor or recipient comprises the modified Zm1d31079 gene or the modified Zm1d44812 gene comprising an expression enhancing element (e.g. transcriptional enhancer). In certain embodiments, methods of making hybrid seed can comprise crossing elite crop maize plant lines where the pollen recipient comprises the modified Zm1d31079 gene or the modified Zm1d44812 gene comprising an expression enhancing element (e.g. transcriptional enhancer) and where the pollen recipient is homozygous for the modified Zm1d31079 gene or the modified Zm1d44812 gene. In certain embodiments, methods of making hybrid seed can comprise crossing elite crop maize plant lines where both the pollen donor and recipient comprise the modified Zm1d31079 gene or the modified Zm1d44812 gene comprising an expression enhancing element (e.g. transcriptional enhancer) and where both the pollen donor and pollen recipient are homozygous for the modified Zm1d31079 gene or the modified Zm1d44812 gene. Methods for hybrid seed production have been disclosed (MacRobert, J. F., P. S. Setimela, J. Gethi, and M. Worku. 2014. Maize Hybrid Seed Production Manual. Mexico, D.F.: CIMMYT) and can be adapted to the production of hybrids disclosed herein. In certain embodiments, the inbred maize plant, the hybrid maize plant, the pollen donor and/or the pollen recipient can each comprise a transgenic locus which confers a trait (e.g., herbicide tolerance or insect resistance such as coleopteran or lepidopteran insects). Transgenes that can be introduced into the maize plant lines comprising a modified Zm1d31079 gene or the modified Zm1d44812 gene by breeding or by direct transformation include: (i) transgenes that confer insect resistance (e.g., transgenes that produce *Bacillus thuringiensis* proteins including Cry1Ab, Cry1Ac, Cry1F, Cry2Ab, Cry2Ae, Cry3A, Cry3Bb, Cry9c, Cry34, Cry35, VIP3A, and variants thereof; transgenes that induce insect-inhibitory RNAi responses); and (ii) transgenes that confer tolerance to distinct herbicides (e.g., CP4-EPSPS or other EPSPS genes which confer glyphosate tolerance; PAT or BAR genes which confer resistance to glufosinate herbicides; aad-1 genes which confer resistance to 2,4-D and aryloxyphenoxypropionate herbicides; DMO genes which confer resistance to dicamba herbicide). Examples of selected transgenic maize plant events which contain transgenes that confer traits such as herbicide tolerance and/or pest tolerance are disclosed in U.S. Pat. Nos. 6,342,660, 7,956,246, 8,575,434, 7,314,970, 8,759,618, 6,852,915, 10316330, 8618358, 8450561, 8686230, 9428765, 8455720, 7897748, 8273959, 8093453, 8502047, and 8466346, which are each incorporated herein by reference in their entireties.

In certain embodiments, maize plants provided herein which comprise a modified Zm1d31079 gene or the modified Zm1d44812 gene can further comprise one or more targeted genetic changes introduced by one or more of gene editing molecules or systems. Such targeted genetic changes include those conferring traits such as improved yield, improved food and/or feed characteristics (e.g., improved oil, starch, protein, or amino acid quality or quantity), improved nitrogen use efficiency, improved biofuel use characteristics, herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control maize plant lacking the targeted genetic change. Types of targeted genetic changes that can be introduced include insertions, deletions, and substitutions of one or more nucleotides in the maize plant genome. Sites in endogenous maize plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous maize plant gene. Non-limiting examples of regulatory sequences which can be inserted into endogenous maize plant genes with gene editing molecules to effect targeted genetic changes which confer useful phenotypes include those set forth in US Patent Application Publication 20190352655, which is incorporated herein by reference in its entirety, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) a microRNA (miRNA) recognition sequence for an engineered miRNA wherein the specific binding agent is the corresponding engineered mature miRNA; (i) a transposon recognition sequence; ( ) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (1) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non-limiting examples of target maize genes that can be subjected to targeted gene edits to confer useful traits include quality and herbicide tolerance traits. In certain embodiments, such targeted genetic changes can be combined with plants which comprise the modified Zm1d31079 gene or the modified Zm1d44812 gene by breeding techniques. Such breeding techniques include crossing and/or introgression by backcrossing to a recurrent parent. In such crosses, the plants which comprise the modified Zm1d31079 gene or the modified Zm1d44812 gene can be either a pollen donor or recipient. In certain embodiments, plants which comprise the modified Zm1d31079 gene or the modified Zm1d44812 gene can be used as the recurrent parent in such backcrosses to introgress the targeted genetic change into plant germplasm comprising the modified Zm1d31079 gene or the modified Zm1d44812 gene. In certain embodiments, plants which comprise the target genetic change(s) can be used as the recurrent parent in such backcrosses to introgress the genomic region comprising the modified Zm1d31079 gene or the modified Zm1d44812 gene into plant germplasm comprising the target genetic change(s).

In certain embodiments, plants provided herein which comprise a modified Zm1d31079 gene or the modified Zm1d44812 gene can further comprise one or more genetic loci conferring traits such as improved yield, improved food and/or feed characteristics (e.g., improved oil, starch, protein, or amino acid quality or quantity), improved nitrogen use efficiency, improved biofuel use characteristics (e.g., improved ethanol production), tolerance to herbicides (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Sources of such genetic loci include elite cultivars, sexually compatible wild or other relatives (e.g., *Zea* sp.), plant germplasm which has been subjected to random mutagenesis (e.g., with a chemical mutagen such as EMS or with gamma-ray mutagenesis), and the like. In certain embodiments, such genetic loci can be combined with plants which comprise the modified Zm1d31079 gene or the modified Zm1d44812 gene by breeding techniques. Such breeding techniques include crossing and/or introgression by backcrossing to a recurrent parent. In such crosses, the plants which comprise modified Zm1d31079 gene or the modified Zm1d44812 gene can be either a pollen donor or recipient. In certain embodiments, plants which comprise the modified Zm1d31079 gene or the modified Zm1d44812 gene can be used as the recurrent parent in such backcrosses to introgress the genetic locus into plant germplasm comprising the genetically altered transcriptional regulatory region. In certain embodiments, plants which comprise the genetic locus or loci can be used as the recurrent parent in such backcrosses to introgress the genomic region comprising modified Zm1d31079 gene or the modified Zm1d44812 gene into plant germplasm comprising the genetic locus or loci.

Also provided herein are methods for producing a commodity plant product or plant material comprising growing any of the aforementioned plants comprising the modified Zm1d31079 gene or the modified Zm1d44812 gene or growing plants from seeds comprising the modified Zm1d31079 gene or the modified Zm1d44812 gene In certain embodiments, such plants and/or seeds are irrigated, fertilized, and/or treated with a biological agent (e.g., a plant beneficial microorganism including a *Bacillus* sp., a *Rhizobium* sp., a *Bradyrhizobium* sp., and the like), nematicide (e.g., a carbamate or organophosphate insecticide), insecticide (e.g., a neonicotinoid, pyrethroid, carbamate, or organophosphate insecticide) and/or fungicide (e.g., a benzimidazole, imidazole, or strobilurin fungicide). Plants can be treated with such fertilizers, biological agents, nematicides, insecticides, and fungicides by methods including spraying, fumigating, and/or soil drenching. Seeds can be treated with such fertilizers, biological agents, nematicides, insecticides, and fungicides by methods including in-furrow applications or by coating (e.g., with a drum coater, rotary coater, tumbling drum, fluidized bed, and/or spouted bed apparatus). Methods and compositions including various binders, fillers, film coats, and active ingredients such as fertilizers, surfactants, plant growth regulators, crop desiccants, fungicides, bacteriocides, bacteriostats, insecticides, and insect repellants for coating seeds that can be adapted for use with seeds provided herein are disclosed in U.S. patent Ser. No. 10/745,578, which is incorporated herein by reference in its entirety.

Embodiments

Various embodiments of the DNA molecules, plants, plant parts, genomes, chromosomes, methods, biological samples, and other compositions described herein are set forth in the following set of numbered embodiments.

1. A maize plant comprising a modified Zm1d31079 gene wherein a heterologous expression enhancing element is located in the modified gene, and wherein the unmodified Zm1d31079 gene comprises the DNA molecule of SEQ ID NO: 1 or an allelic variant thereof.
2. The maize plant of embodiment 1, wherein the modified Zm1d31079 gene and/or the unmodified Zm1d31079 gene encode the Zm1d31079 protein of SEQ ID NO: 2 or an allelic variant thereof.
3. The maize plant of embodiment 1 or 2, wherein the modified Zm1d31079 gene is located in the native chromosomal location of the unmodified Zm1d31079 gene.
4. The maize plant of embodiment 1 or 2, wherein the modified Zm1d31079 gene comprises a transgene located in a chromosomal location other than in the native chromosomal location of the unmodified Zm1d31079 gene.
5. A maize plant comprising a modified Zm1d44812 gene wherein a heterologous expression enhancing element is located in the modified gene, and wherein the unmodified Zm1d44812 gene comprises the DNA molecule of SEQ ID NO: 8 or an allelic variant thereof, and wherein the modified Zm1d44812 gene is located in the native chromosomal location of the unmodified Zm1d44812 gene.
6. The maize plant of embodiment 5, wherein the modified Zm1d44812 gene and/or the unmodified Zm1d44812 gene encode the Zm1d44812 protein of SEQ ID NO: 9 or an allelic variant thereof.
7. The maize plant of embodiment 5 or 6, wherein expression of a Zm1d44812 gene product in a plant having the modified Zm1d44812 gene is respectively increased by about 5% to 10% or 20% in at least one tissue in the maize plant in comparison to a control maize plant lacking the modified Zm1d44812 gene.
8. The maize plant of embodiment 5, 6, 7, or 8, wherein the height of the maize plant is reduced in comparison to a control maize plant lacking the lacking the modified Zm1d44812 gene, optionally wherein the height is reduced by about 5% or 10% to about 15%, 20%, 30%, or 50% in comparison to a control maize plant lacking the modified Zm1d44812 gene.
9. The maize plant of any one of embodiments 1-8, wherein the heterologous expression enhancing element comprises: (i) a heterologous transcription enhancer, a heterologous translational enhancing element, and/or a heterologous intron; or (ii) a heterologous promoter, heterologous 5' UTR, and/or heterologous intron.
10. The maize plant of embodiment 9, wherein the heterologous transcription enhancer is located in the promoter, the 5' untranslated region (5' UTR), an intron, a 3' untranslated region (3' UTR), or a 3' flanking region of the modified Zm1d31079 gene or the modified Zm1d44812 gene.
11. The maize plant of embodiment 9 or 10, wherein the heterologous transcription enhancer comprises a DNA molecule set forth in SEQ ID NO: 16, 17, SEQ ID NO: 19-124, and/or 125.
12. The maize plant of embodiment 9, 10, or 11, wherein the transcription enhancer is located about 10, 20, 30, 40, 100, or 150 base pairs (bp) to about 200, 240, 300, 350, 400, 500, or 1000 bp 5' of the transcriptional start site (TSS) of the Zm1d31079 or Zm1d44812 gene.
13. The maize plant of embodiment 9, wherein the transcription enhancer comprises SEQ ID NO: 16, 17, 19-124, and/or 125 and the insertion is located:

(i) about 116 to about 96 base pairs or about 106 base pairs 5' to the TSS of the Zm1d31079 gene;
(ii) about 119 to about 99 base pairs or about 109 base pairs 5' to the TSS of the Zm1d31079 gene;
(iii) about 170 to about 150 base pairs or about 160 base pairs 5' to the TSS of the Zm1d31079 gene;
(iv) about 252 to about 232 base pairs or about 242 base pairs 5' to the TSS of the Zm1d31079 gene;
(v) about 261 to about 241 base pairs or about 251 base pairs 5' to the TSS of the Zm1d31079 gene;
(vi) in a double stranded break introduced in the Zm1d31079 promoter with a Cas9 nuclease and a guide RNA encoded by SEQ ID NO: 4, 5, or 6; or
(vii) in a double stranded break introduced in the Zm1d31079 promoter with a Cas12 nuclease and a guide RNA encoded by SEQ ID NO: 3 or 7.

14. The maize plant of embodiment 9 wherein the transcription enhancer comprises SEQ ID NO: 16, 17, 19-124, and/or 125 and the insertion is located:

(i) about 85 to about 65 base pairs or about 75 base pairs 5' to the TSS of the Zm1d44812 gene;
(ii) about 93 to about 73 base pairs or about 83 base pairs 5' to the TSS of the Zm1d44812 gene;
(iii) about 183 to about 163 base pairs or about 173 base pairs 5' to the TSS of the Zm1d44812 gene;
(iv) about 188 to about 168 base pairs or about 178 base pairs 5' to the TSS of the Zm1d44812 gene;
(v) about 269 to about 249 base pairs or about 259 base pairs 5' to the TSS of the Zm1d44812 gene;
(vi) in a double stranded break introduced in the Zm1d44812 promoter with a Cas9 nuclease and a guide RNA encoded by SEQ ID NO: 10, 12, or 15; or (vii) in a double stranded break introduced in the Zm1d44812 promoter with a Cas12 nuclease and a guide RNA encoded by SEQ ID NO: 11, 13, or 14.

15. The maize plant of embodiment 9, wherein the heterologous intron is located in the 5' UTR and/or within the coding region of the modified Zm1d31079 gene or the modified Zm1d44812 gene, optionally wherein the intron is located within about 500, 200, 100, 50, 30, or 20 base pairs of the transcription start site (TSS).

16. The maize plant of embodiment 15, wherein the heterologous intron comprises a UBQ, EF-1α, EF-1P, Histone H3, ATPK1, RHD3, or MHX intron, optionally wherein the UBQ, EF-1α, EF-1P, Histone H3, ATPK1, RHD3, or MHX intron comprises a rice or maize intron.

17. The maize plant of embodiment 9, wherein the heterologous translational enhancer is located in the 5' UTR and/or within the coding region of the modified Zm1d31079 gene or the modified Zm1d44812 gene.

18. The maize plant of embodiment 17, wherein the translational enhancer is encoded by a DNA molecule comprising the DNA sequence of a rice alcohol dehydrogenase (OsAdh), glutathione transferase U50 (OsGst U50), glutathione peroxidase 1 (OsGsp 1), 20S proteasome alpha1 subunit (Os20Sα1), pathogenesis-related protein 4b (OsPrp4b), glycine-rich cell-wall structural protein 1 (OsGrcwp1), or UspA domain containing protein (OsUspA) 5'UTR and wherein all or part of said OsAdh, Os GstU50, Os20Sα1, OsPrp4b, Os Grcwp1, or OsUspA 5'UTR is substituted for all or part of the Zm1d31079 5' UTR or the Zm1d44812 5' UTR in the modified Zm1d31079 or the modified Zm1d44812 gene.

19. The maize plant of any one of embodiments 1 to 18, wherein expression of the Zm1d31079 or Zm1d44812 gene is increased in at least one tissue of the maize plant in comparison to a control maize plant lacking the modified Zm1d31079 gene or the modified Zm1d44812 gene, optionally wherein expression of the Zm1d31079 or Zm1d44812 gene is increased in at least stalk tissue.

20. The maize plant of any one of embodiments 1 to 19, wherein height of the maize plant is reduced in comparison to a control maize plant lacking the lacking the modified Zm1d31079 gene or the modified Zm1d44812 gene, optionally wherein the height is reduced by about 5% or 10% to about 15%, 20%, 30%, or 50% in comparison to a control maize plant lacking the modified Zm1d31079 gene or the modified Zm1d44812 gene.

21. The maize plant of any one of embodiments 1 to 20, wherein the maize plant is a hybrid maize plant which is heterozygous for the modified Zm1d31079 or the modified Zm1d44812 gene.

22. The maize plant of any one of embodiments 1 to 21, wherein expression of a Zm1d31079 gene product or a Zm1d44812 gene product in a plant having the modified Zm1d31079 gene or the modified Zm1d44812 gene is respectively increased by about 20% to 80% in at least one tissue in the maize plant in comparison to a control maize plant lacking the modified Zm1d31079 gene or the modified Zm1d44812 gene.

23. The maize plant of any one of embodiments 1 to 21, wherein expression of a Zm1d31079 gene product or a Zm1d44812 gene product in a plant having the modified Zm1d31079 gene or the modified Zm1d44812 gene is increased by about 1.2-fold or 1.5-fold to about 2-fold, 3-fold, or 5-fold in at least one maize tissue in the maize plant in comparison to a control maize plant lacking the modified Zm1d31079 gene or the modified Zm1d44812 gene.

24. A maize plant part comprising the modified Zm1d31079 gene or the modified Zm1d44812 gene of any one of embodiments 1 to 23.

25. The maize plant part of embodiment 24, wherein the part is a seed, stalk, stem, or leaf.

26. The maize plant part of embodiment 25, wherein the seed further comprises at least a partial coating of a composition comprising a biological agent, nematicide, insecticide, or fungicide.

27. The maize plant part of embodiment 25 or 26, wherein the maize plant seed is a hybrid maize plant seed which is heterozygous for the modified Zm1d31079 or the modified Zm1d44812 gene.

28. A method of producing maize seed, comprising growing the maize plant of any one of embodiments 1 to 23 and harvesting seed therefrom.

29. A method of producing hybrid maize seed comprising crossing a maize plant homozygous for the modified Zm1d31079 gene set forth in any one of embodiments 1 to 4, 9-13, or 15-23 to another maize plant homozygous for the modified Zm1d31079 gene and harvesting seed from a pollen recipient of the cross.

30. A method of producing hybrid maize seed comprising crossing a maize plant homozygous for the modified Zm1d44812 gene set forth in any one of embodiments 5 to 12 or 14 to 23 to another maize plant homozygous for the modified Zm1d44812 gene and harvesting seed from a pollen recipient of the cross.

31. A method of producing inbred maize seed comprising selfing: (i) a maize plant homozygous for the modified Zm1d31079 gene set forth in any one of embodiments 1 to 4, 9-13, or 15-23; or (ii) a maize plant homozygous for the modified Zm1d44812 gene set forth in any one of embodiments 5 to 12 or 14 to 23.

32. A method of producing a maize plant comprising an added desired trait, said method comprising introducing a transgene, a targeted genetic change, and/or a genetic locus conferring the desired trait into the maize plant of any one of embodiments 1 to 23.

33. A method of producing a commodity maize plant product, said method comprising: (i) processing a maize plant of any one of embodiments 1 to 23 or a maize seed obtained therefrom; and (ii) recovering the commodity maize plant product from the processed maize plant or maize seed.

34. The method of embodiment 33, wherein the commodity maize plant product is seed meal, starch, syrup, silage, oil, or protein.

35. The method of embodiment 33, wherein the commodity maize plant product comprises a detectable amount of a DNA molecule comprising the heterologous transcription enhancer, the heterologous translational enhancing element, and/or the heterologous intron located in a DNA fragment of the modified Zm1d31079 gene or in a DNA fragment of the modified Zm1d44812 gene.

36. A biological sample comprising a detectable amount of a DNA molecule comprising a heterologous transcription enhancer, a heterologous intron, and/or heterologous translational enhancing element located in a DNA fragment of a modified Zm1d31079 gene or in a DNA fragment of a modified Zm1d44812 gene.

37. The biological sample of embodiment 36, wherein the biological sample comprises material obtained from the maize plant of any one of embodiments 1 to 23 or a part thereof, wherein the part is optionally a seed or is optionally a part of embodiment 24-27.

38. The biological sample of embodiment 37, wherein the biological sample is non-regenerable.

39. The biological sample of embodiment 37, wherein the biological sample comprises maize seed meal.

40. A method of making a maize plant of any one of embodiments 1 to 3 or 5 to 23, comprising:

(a) contacting a maize plant genome with gene editing molecules comprising a first site-specific nuclease which introduces a double stranded DNA break in a promoter region, a 5' UTR, a coding region, a 3' UTR, or a 3' flanking region in: (i) an unmodified Zm1d31079 gene comprising the DNA molecule of SEQ ID NO: 1 or an allelic variant thereof, or (ii) an unmodified Zm1d44812 gene comprising the DNA molecule of SEQ ID NO: 8 or an allelic variant thereof, and a donor DNA template or other DNA template comprising a heterologous expression enhancing element; and (b) selecting a maize plant comprising a modified Zm1d31079 gene or a modified Zm1d44812 gene, wherein the modified Zm1d31079 gene or the modified Zm1d44812 gene comprises an insertion of the heterologous expression enhancing element in the promoter region, the 5' UTR, the coding region, the 3' UTR, or the 3' flanking region of the gene, wherein expression of the modified Zm1d31079 gene or a modified Zm1d44812 gene is increased in at least one tissue, and wherein height of the maize plant comprising the modified Zm1d31079 gene or the modified Zm1d44812 gene is decreased in comparison to a control maize plant lacking the modified Zm1d31079 gene or the modified Zm1d44812 gene.

41. The method of embodiment 40, wherein the heterologous expression enhancing element comprises a heterologous transcription enhancer, a heterologous translational enhancing element, and/or a heterologous intron.

42. The method of embodiment 40 or 41, wherein the double stranded break is introduced in the promoter, the 5' untranslated region (5' UTR), an intron, a 3' untranslated region (3' UTR), or a 3' flanking region of the unmodified Zm1d31079 gene or the unmodified Zm1d44812 gene and the donor DNA template or other DNA template comprises the heterologous transcription enhancer.

43. The method of embodiment 42, wherein the transcription enhancer comprises a DNA molecule set forth in SEQ ID NO: 16, 17, 19-124, and/or SEQ ID NO: 125.

44. The method of embodiment 40, wherein the double stranded break is introduced about 10, 20, 30, 40, 100, or 150 base pairs (bp) to about 200, 240, 300, 350, 400, 500, or 1000 bp 5' of the transcriptional start site (TSS) of the Zm1d31079 or Zm1d44812 gene.

45. The method of embodiment 44, wherein the transcription enhancer comprises SEQ ID NO: 16, 17, 19-124, and/or 125 and the double stranded break is introduced:

(i) about 116 to about 96 base pairs or about 106 base pairs 5' to the TSS of the Zm1d31079 gene;

(ii) about 119 to about 99 base pairs or about 109 base pairs 5' to the TSS of the Zm1d31079 gene;

(iii) about 170 to about 150 base pairs or about 160 base pairs 5' to the TSS of the Zm1d31079 gene;

(iv) about 252 to about 142 base pairs or about 242 base pairs 5' to the TSS of the Zm1d31079 gene;

(v) about 261 to about 241 base pairs or about 251 base pairs 5' to the TSS of the Zm1d31079 gene;

(vi) in the Zm1d31079 promoter with a Cas9 nuclease and a guide RNA encoded by SEQ ID NO: 4, 5, or 6; or (vii) in the Zm1d31079 promoter with a Cas12 nuclease and a guide RNA encoded by SEQ ID NO: 3 or 7.

46. The method of embodiment 44, wherein the transcription enhancer comprises SEQ ID NO: 16, 17, 19-124, and/or 125 and the double stranded break is introduced:

(i) about 85 to about 65 base pairs or about 75 base pairs 5' to the TSS of the Zm1d44812 gene;

(ii) about 93 to about 73 base pairs or about 83 base pairs 5' to the TSS of the Zm1d44812 gene;

(iii) about 183 to about 163 base pairs or about 173 base pairs 5' to the TSS of the Zm1d44812 gene;

(iv) about 188 to about 168 base pairs or about 178 base pairs 5' to the TSS of the Zm1d44812 gene;

(v) about 269 to about 249 base pairs or about 259 base pairs 5' to the TSS of the Zm1d44812 gene;

(v) in the Zm1d44812 promoter with a Cas9 nuclease and a guide RNA encoded by SEQ ID NO: 10, 12, or 15; or (vi) in the Zm1d44812 promoter with a Cas12 nuclease and a guide RNA encoded by SEQ ID NO: 11, 13, or 14.

47. The method of embodiment 41, wherein the DNA donor or other DNA template comprises a heterologous translational enhancer and the double stranded break is introduced in the 5' UTR and/or within the coding region of the unmodified Zm1d31079 gene or the unmodified Zm1d44812 gene.

48. The method of embodiment 47, wherein the translational enhancer is encoded by a DNA molecule comprising the DNA sequence of a rice alcohol dehydrogenase (OsAdh), glutathione transferase U50 (OsGst U50), glutathione peroxidase 1 (OsGsp 1), 20S proteasome alpha1 subunit (Os20Sα1), pathogenesis-related protein 4b (OsPrp4b), glycine-rich cell-wall structural protein 1 (Os Grcwp1), or UspA domain containing protein (OsUspA) 5'UTR and wherein all or part of said OsAdh, Os GstU50, Os20Sα1, OsPrp4b, OsGrcwp1, or OsUspA 5'UTR is substituted for all or part of the Zm1d31079 or the Zm1d44812 5' UTR in the modified Zm1d31079 or the modified Zm1d44812 gene.

49. The method of embodiment 41, wherein the DNA donor or other DNA template comprises a heterologous intron and the double stranded break is introduced in the 5' UTR and/or within the coding region of the modified Zm1d31079 gene or the modified Zm1d44812 gene, optionally wherein the double stranded break is introduced within about 500, 200, 100, 50, 30, or 20 base pairs of the TSS.

50. The method of embodiment 49, wherein the heterologous intron comprises a UBQ10, EF-1α, EF-1β, Histone H3, ATPK1, RHD3, or MHX intron, optionally wherein the UBQ10, EF-1α, EF-1β, Histone H3, ATPK1, RHD3, or MHX intron comprises a rice or maize intron.

51. A method of making a maize plant of any one of embodiments 1-2 or 4-23, comprising:

(a) contacting a maize plant genome with a transgene comprising a modified Zm1d31079 gene, wherein the modified Zm1d31079 gene comprises a heterologous promoter, heterologous 5' UTR, and/or heterologous intron which is operably linked to a coding region encoding the Zm1d31079 protein of SEQ ID NO: 2 or an allelic variant thereof; and (b) selecting a transgenic maize plant comprising the modified Zm1d31079 gene, wherein expression of the modified Zm1d31079 gene is increased in at least one tissue and wherein height of the maize plant is decreased in comparison to a control maize plant lacking the modified Zm1d31079 gene.

52. The method of embodiment 51, wherein the promoter is a ubiquitin promoter, an actin promoter, or a plant viral promoter, optionally wherein the plant viral promoter comprises a caulimovirus promoter.

53. The method of embodiment 51, wherein the heterologous intron comprises a UBQ, EF-1α, EF-1β, Histone H3, ATPK1, RHD3, or MHX intron, optionally wherein the UBQ, EF-1α, EF-1P, Histone H3, ATPK1, RHD3, or MHX intron comprises a rice or maize intron.

EXAMPLES

Example 1. Insertion of a Transcription Enhancer in the Zm1d31079 (SEQ ID NO: 1) and Zm1d44812 (SEQ ID NO: 8) Promoters Maize genes Zm1d31079 (SEQ ID NO: 1) and Zm1d44812 (SEQ ID NO: 8) were targeted for insertion of a transcription enhancer (SEQ ID NO: 16) to increase expression of the genes and decrease maize plant height. Guide RNAs were designed at different distances of the transcriptional start sites (TSS) of the genes in order to create an allelic series and assess whether increasing the distance to the TSS would result in milder phenotypes for plant height. Summaries of the guide RNAs designed for the two genes are provided in Tables 2 and 3.

TABLE 2

Zm1d31079 guide RNA design

| gRNA name | SEQ ID NO: | DNA sequence that encodes spacer element of gRNA | Distance to TSS | Nuclease |
|---|---|---|---|---|
| Zm1d31079 Pro-106 | 3 | tgcacctgcttctgccacatggc | 106 | CasS[1] |
| Zm1d31079 Pro-109 | 4 | ctgcacctgcttctgccaca | 109 | CasB[2] |
| Zm1d31079 Pro-160 | 5 | aattaatgcagcgtcggaat | 160 | CasB |
| Zm1d31079 Pro-242 | 6 | ctgtttgggcaaccgccatg | 242 | CasB |
| Zm1d31079 Pro-251 | 7 | ggcaaccgccatgagggcagggc | 251 | CasS |

[1]Cas nuclease which provides a staggered cut.

[2]Cas nuclease which provides a blunt cut.

TABLE 3

Zm1d44812 guide RNA design

| gRNA | SEQ ID NO: | Sequence | Distance to TSS | Nuclease |
|---|---|---|---|---|
| Zm1d44812 Pro-75 | 10 | actgcacactccccgacacg | 75 | CasB |
| Zm1d44812 Pro-83 | 11 | cagttacacccctcccctccccc | 83 | CasS |
| Zm1d44812 Pro-173 | 12 | acctttggataaatgacagc | 173 | CasB |
| Zm1d44812 Pro-178 | 13 | ctgtcaacaatcctagctccagc | 178 | CasS |
| Zm1d44812 Pro-249 | 14 | accccaaattggatccctttcat | 249 | CasS |
| Zm1d44812 Pro-259 | 15 | taaatgaaagggatccaatt | 259 | CasB |

Immature embryos of a transgenic B104 "editor" maize line constitutively overexpressing a CasB nuclease polypeptide were harvested 13 days after pollination and transformed by biolistics with: a plasmid containing herbicide and visual selection markers (p35S::pat::tNOS and pZmUbi::mScarlet::tZmUbi), a single guide RNA for the CasB nuclease comprising one of the indicated spacers (Zm1d31079_Pro-109, Zm1d44812_Pro-75, Zm1d31079_Pro-242, or Zm1d44812_Pro-259), and DNA of the 3× enhancer (/5Phos/G*T*AAGCGCTT-ACGTAAGCGCTTACGTAAGCGCTT*A*C; SEQ ID NO: 18; * is a phosphorothioate bond) for NHEJ insertion. The guide RNA and DNA were from Integrated DNA Technologies (Coralville, IA, USA). Callus was induced, the transformed cells selected, and transformed TO generation plants regenerated by conventional methods. The following plants in Table 4 were regenerated in TO and selected for further characterization.

TABLE 4

Transformation Results

| T0 Line (gRNA) | Plants recover |
|---|---|
| ZM185 (Zmd31079_Pro-109) | 1 event, 2 plants |
| ZM186 (Zmd31079-Pro-109) | 1 event, 3 plants |
| ZM187 (Zm1d44812_Pro-75) | 1 event, 4 plants |
| ZM200 (Zm1d31079_Pro-242) | 7 events, 7 plants |
| ZM202 (Zm1d31079_Pro-242) | 2 events, 5 plants |
| ZM203 (Zm1d44812_Pro-259) | 2 event, 7 plants |

DNA fragments encompassing the targeted sites were PCR-amplified, and the presence of an insert in the edited T0 plants was observed. The edited plants were observed to have diminished height at the TO stage. FIGS. 3, 4, 5, 6, 7, and 8 show the difference between T0 plants comprising the enhancer insertions in the Zm1d31079 or Zm1d44812 promoters and control plants lacking the insertions in those promoters. The control plants were edited T0 plants at the similar development stage but bearing edits in genes unrelated to plant height.

Example 2. Further Analysis of Plants Comprising an Insertion of a Transcription Enhancer in the Zm1d31079 (SEQ ID NO: 1) and Zm1d44812 (SEQ ID NO: 8) Promoters T0 plants such as those described in Example 1 are backcrossed to a B104 wild type. The resulting T1 plants are analyzed for the presence/absence of the enhancer at the target site and T1 plants are grown and subjected to phenotypic analysis, using siblings lacking the enhancer insertion as controls and focusing on plant height and general plant development. Selected T1 plants are crossed to a different genotype (e.g. PHRO3) to produce hybrid F1 seed, the resulting F1 plants are subjected to a phenotypic analysis comprising quantitative height component measurements. In addition, molecular analysis is performed where relevant to measure the changes in expression levels of the target Zm1d31079 and Zm1d44812 genes.

Example 3. Analysis of Plants Comprising an Insertion of a Triplicated ZmOCS Transcription Enhancer in the Zm1d31079 Promoter Two lines were created with triplicated ZmOCS enhancer element (SEQ ID NO: 16) insertions in the promoter of the Zm1d31079 (SEQ ID NO: 1) gene: one with the triplicated ZmOCS enhancer inserted at 109 bases upstream of the transcription start site (TSS) of the Zm1d31079 gene, and one with the triplicated ZmOCS enhancer inserted at 242 bases upstream of the TSS of the Zm1d31079 gene. Expression in young shoot apices showed that insertion of the enhancer led to higher expression of Zm1d31079 in both lines, with a stronger effect in individuals homozygous for the enhancer compared to heterozygous individuals (FIG. 9). For each, T2 individuals homozygous or heterozygous for the triplicated ZmOCS enhancer insertion were grown in the greenhouse and compared to segregating siblings that did not contain the enhancer insertion. Genotypes were spaced out to avoid shading effects. Plant height (from soil to collar of the youngest leaf) was measured regularly throughout development (FIG. 10), and plant height (from soil level to the collar of the flag leaf) and ear height (from soil level to the base of the ear) were measured at maturity, showing that the presence of the triplicated ZmOCS enhancer in both cases led to a statistically significant decrease in both plant height and ear height (Table 5). In both lines for which triplicated ZmOCS enhancer insertion heterozygotes were phenotyped, the effect on plant height was weaker compared to triplicated ZmOCS enhancer insertion homozygotes (Table 5; FIG. 10).

TABLE 5

Plant height and ear height for two lines segregating for triplicated ZmOCS enhancer insertions in the Zm1d31079 promoter.

| Line | Plant height (cm)[1] | Ear height (cm)[1] |
|---|---|---|
| −109 segregating control (no enhancer) | 180.1 ± 5.4 | 94.0 ± 5.7 |
| −109 3x ZmOCS enhancer (homozygous) | 129.7 ± 9.4 *** | 56.9 ± 6.9 *** |
| −242 segregating control (no enhancer) | 167.6 ± 11.4 | 79.7 ± 6.6 |
| −242 3x ZmOCS enhancer (homozygous) | 140.2 ± 7.3 *** | 57.3 ± 5.2 *** |
| −109 segregating control (no enhancer) | 181.8 ± 9.3 | 91.4 ± 5.2 |
| −109 3x ZmOCS enhancer (heterozygous) | 169.3 ± 9.7 * | 81.4 ± 4.1 ** |
| −242 segregating control (no enhancer) | 170.9 ± 11.2 | 80.5 ± 6.3 |
| −242 3x ZmOCS enhancer (heterozygous) | 155.3 ± 7.7 * | 70.5 ± 6.7 * |

[1]Average ± standard deviation is shown, with N = 5-8 per group. Statistical significance is indicated by asterisks (*, $p < 0.05$; , $p < 0.01$; *, $p < 0.001$; p-value calculated as effect of genotype in linear model).

The breadth and scope of the present disclosure should not be limited by any of the above-described exemplary embodiments but should be defined only in accordance with the following claims and their equivalents.

What is claimed is:

1. A maize plant comprising a modified maize gene wherein the unmodified maize gene comprises the DNA molecule of SEQ ID NO: 1 or an allelic variant thereof having at least 95% sequence identity to SEQ ID NO: 1, wherein the modified maize gene comprises an insertion of a heterologous transcription enhancer into the promotor of unmodified maize gene of SEQ ID NO: 1 or allelic variant thereof, wherein the unmodified maize gene or the unmodified allelic variant thereof does not contain the heterologous transcription enhancer, and wherein the modified maize gene is located in the native chromosomal location of the unmodified maize gene of SEQ ID NO: 1.

2. The maize plant of claim 1, wherein the modified maize gene and the unmodified maize gene encodes the maize protein of SEQ ID NO: 2 or an allelic variant thereof having at least 95% sequence identity to SEQ ID NO: 2.

3. The maize plant of claim 1, wherein the heterologous transcription enhancer comprises a DNA molecule set forth in SEQ ID NO: 16 and/or 17.

4. The maize plant of claim 1, wherein the transcription enhancer is located at a position from 10, base pairs (bp) to 1000 bp 5' of the transcriptional start site (TSS) of the maize gene located at nucleotide 1911 of SEQ ID NO:1.

5. The maize plant of claim 1, wherein the transcription enhancer comprises SEQ ID NO: 16 or 17 and the insertion is located at a position:

(i) from 96 base pairs to 116 base pairs 5' to the TSS of the unmodified maize gene located at nucleotide 1911 of SEQ ID NO:1;

(ii) from 99 base pairs to 119 base pairs 5' to the TSS of the unmodified maize gene located at nucleotide 1911 of SEQ ID NO:1;

(iii) from 150 base pairs to 170 base pairs 5' to the TSS of the unmodified maize gene located at nucleotide 1911 of SEQ ID NO:1;

(iv) from 232 base pairs to 252 base pairs 5' to the TSS of the unmodified maize gene located at nucleotide 1911 of SEQ ID NO:1;

(v) from 241 base pairs to 261 base pairs 5' to the TSS of the unmodified maize gene located at nucleotide 1911 of SEQ ID NO:1;

(vi) in a double stranded break introduced in the promoter with a Cas9 nuclease and a guide RNA encoded by SEQ ID NO: 4, 5, or 6; or (vii) in a double stranded break introduced in the promoter with a Cas12 nuclease and a guide RNA encoded by SEQ ID NO: 3 or 7.

6. The maize plant of claim 1, wherein the height of the maize plant is reduced in comparison to a control maize plant lacking the modified maize gene, optionally wherein the height is reduced by 5% to 20% in comparison to a control maize plant lacking the modified maize gene.

7. The maize plant of claim 1, wherein the maize plant is a hybrid maize plant which is heterozygous for the modified maize gene.

8. The maize plant of claim 1, wherein expression of the maize gene product in the maize plant having the modified maize gene is increased by 1.2-fold to 5-fold or by 20% to 80% in at least one maize tissue in the maize plant in comparison to a control maize plant lacking the modified maize gene.

9. A maize plant part comprising the modified maize gene of claim 1.

10. A method of producing hybrid maize seed comprising crossing a maize plant homozygous for the modified maize gene set forth in claim 1 to another maize plant homozygous for the modified maize gene and harvesting seed from a pollen recipient of the cross.

11. A method of producing a commodity maize plant product, said method comprising: (i) processing the maize plant of claim 1 or a maize seed obtained therefrom; and (ii) recovering the commodity maize plant product from the processed maize plant or maize seed, wherein the commodity maize plant product comprises a detectable amount of a DNA molecule comprising the heterologous transcription enhancer located in a DNA fragment of the modified maize gene.

12. A biological sample comprising a detectable amount of a DNA molecule comprising a heterologous transcription enhancer located in a DNA fragment comprising the promoter of a modified maize gene, wherein the unmodified maize gene or the unmodified allelic variant thereof does not contain the heterologous transcription enhancer, and wherein the promoter of the unmodified maize gene comprises nucleotides 1 to 1910 of SEQ ID NO:1 or an allelic variant thereof having at least 95% sequence identity to nucleotides 1 to 1910 of SEQ ID NO: 1.

13. A method of making the maize plant of claim 1, comprising:

(a) contacting a maize plant genome with gene editing molecules comprising a first site-specific nuclease which introduces a double stranded DNA break in a promoter region, in an unmodified maize gene comprising the DNA molecule of SEQ ID NO: 1 or an allelic variant thereof having at least 95% sequence identity to SEQ ID NO: 1; and a donor DNA template or other DNA template comprising a heterologous transcription enhancer; and (b) selecting a maize plant comprising a modified maize gene, wherein the modified maize gene comprises an insertion of the heterologous transcription enhancer in the promoter region of the gene, wherein expression of the modified maize gene is increased in at least one tissue, and wherein height of the maize plant comprising the modified maize gene is decreased in comparison to a control maize plant lacking the modified maize.

14. The method of claim 13, wherein the transcription enhancer comprises a DNA molecule set forth in SEQ ID NO: 16 and/or 17.

15. The method of claim 14, wherein the transcription enhancer comprises SEQ ID NO: 16 or 17 and the double stranded break is introduced:

(i) from 96 base pairs to 116 base pairs 5' to the TSS of the unmodified maize gene located at nucleotide 1911 of SEQ ID NO:1;

(ii) from 99 base pairs to 119 base pairs 5' to the TSS of the unmodified maize gene located at nucleotide 1911 of SEQ ID NO:1;

(iii) from 150 base pairs to 170 base pairs 5' to the TSS of the unmodified maize gene located at nucleotide 1911 of SEQ ID NO:1;

(iv) from 142 base pairs to 252 base pairs 5' to the TSS of the unmodified maize gene located at nucleotide 1911 of SEQ ID NO:1;

(v) from 241 base pairs to 261 base pairs 5' to the TSS of the unmodified maize gene located at nucleotide 1911 of SEQ ID NO:1;

(vi) in the promoter with a Cas9 nuclease and a guide RNA encoded by SEQ ID NO: 4, 5, or 6; or (vii) in the promoter with a Cas12 nuclease and a guide RNA encoded by SEQ ID NO: 3 or 7.

* * * * *

SEQUENCE LISTING

```
Sequence total quantity: 125
SEQ ID NO: 1          moltype = DNA  length = 2773
FEATURE               Location/Qualifiers
```

```
source                  1..2773
                        mol_type = genomic DNA
                        organism = Zea mays
SEQUENCE: 1
ggataaatag ggattggagt ggattgaagt gtattttagg tattgaaagg gaaattagtt  60
tatattacac ttcaatacac cttataccac ctcaatccac tccaatccaa gattacccaa  120
acaaacccta agggcttgtt cgctttggag tggattgagg gggattggag gggattaaat  180
cccctcctat acaaatttgt ataggagggg atttaatccc ctccaatccc cctcaatcca  240
ctccaaagcg aacaagccct aagggggatt ggaggggatt caatcccctt ctatataaat  300
ttgtatagaa gtggattgaa tcccctctaa tccccctcaa tccactccta accgaacagg  360
gccttagggg tggtgacata cgtgtcccct ccccgctaag aagtggcact gacccctact  420
caatctacat gggcttttta acctcacttc ctcccacgtc gcgaccgaga tcctggctac  480
caacaacttt cacgctattc aatctacatg gttcttgtgt ccatgaggga ttatgggaag  540
gagagataga tttgtttata atcgaaggga gaaggggagt gccattgcat tatatctaga  600
tacatatata catataataa taatgcattt gaaaaggcca aaccctcgat cgtgtaattc  660
aaaacaaaga tagtactata ctatatatat gcatgtcatg gctctccagc agtttaccca  720
tcctatctcc tcctatatca tattcgactt caaatttcac tcagtcaaca acagtacagg  780
ctatgatgca aaacattgcg ggcagtctaa tagctacaca tatgggacac catacccaca  840
ccaagaatcg tctcattctt ttttcttaac tcggaactac attaatgagt tcccaacttg  900
caactctctt gtgaagtttc agtgctcttt caatgacgtg aactgttctc gctccgaaag  960
gaggaagctg ataacgagga gagcccatca taaccggttg gagtaagcaa ccaaactcga  1020
tcagcatcat ggggtcacca tcactcggta accaaattgc tctcgagcta agctagctag  1080
cttgttgcaa gatcgagtcg tcatgcaaac ttcgagcttg gcttgggcgt cttgttaaca  1140
gactttcccc actgtttccc acgacctcac tctaattgga tgcacacaag ttataataat  1200
gcatatatag atatagatat atctggctgt ttagactgct gcagcgctat agctaaggaa  1260
atgtatgtag ataaaaggcg cacacatata tttgaacggc atatgttaat aaaactacct  1320
cctgtatttt ctttctttct ttttcaatat atatgtcgaa ggaaatggtg ccgtggaacg  1380
tccgacacga catgtggagg gagctgcagc gctacagcaa cgcatatacg cgcaccatga  1440
gtgtgatgtt gattagcgcc accgtaccac cacctgtgat ctctgtggca gtatatataa  1500
tataatataa tataatataa tataatataa tataatataa tataatataa tataatataa  1560
tataataatc accccccatg catgcagcca gcttttggtt ttcgggcgcc aaaatgagcc  1620
tgcgtgcttg tcgtcttcct gcaggcccct tgcttgccct gccctcatgg cggttgccca  1680
aacagcgcgg gggcgggggg cgggccccgc cgctgccagt tcgccgcttc aataattaat  1740
gcagcgtcgg aattggggcg tggtgggctt gccatttctg atttctgcac ctgcttctgc  1800
cacatggccg tcgtcgtaac ctccttctcc tcctcctaaa gctagctagc tagctagtac  1860
tcgtgtacct gcaagtgtta tatagtagga gtagcacctc ctccaccaat cgcgcgcaca  1920
cacacaccca gcttagctca gctcaggtag ctatagctag agagctggac gaccctcgcg  1980
cgacctcaga tagattttta atggaggcgc cagcagcgcc acctccgtcg tacgacggcg  2040
gcggcggcgg cggctacgtc ctcgtcgacc tgtccctgac gctgggcccg accgcgacgc  2100
cacaccctgc ctcctcctcc tctcctgagc ctgaccacac accagccgcc gccgccgccg  2160
gttccagttc cgccggcgtg cggctgttcc cgtgcctctt ctgcaacaag aagttcctca  2220
agtcgcaggc gctcggcggc caccagaacg cgcacaagaa ggagaggagc gtggggtgga  2280
acgcccacct ctacctcccg ccgccggccg cggacacggc gtcggcgtcg gtcgccggcg  2340
gcgccgccgc tcgtgccgcg acgacgcccg tcggcagcag ccacgcgctg ccgatgatcc  2400
aggccgtctc gcactcgtgc caccaccatg agcaccacca ccgggacggc ggcgcggcgg  2460
cgccgttgtt ggagacggcg tggtggtcgt cgtgcgcgga ggagaaacag cagaggcacc  2520
ccgttgacct caatctcagg ctctagctgc tagcgctgtc atatcccctg cttgtgtgcg  2580
taatatataa atcctgaagg agtacgtaac gtaccgtacg tgctgtcgag gtagggtgag  2640
gcgtctcggt gtgcctgtgc aaaagcgtgc gaggcccatg ggccatggcc cagcattcta  2700
tgattatgtg tcgtcgcaac gagcacgcac actttatagt tttatggtgc caattatatg  2760
cctctttatt tca                                                     2773

SEQ ID NO: 2            moltype = AA  length = 181
FEATURE                 Location/Qualifiers
source                  1..181
                        mol_type = protein
                        organism = Zea mays
SEQUENCE: 2
MEAPAAPPPS YDGGGGGGYV LVDLSLTLGP TATPHPASSS SPEPDHTPAA AAAGSSSAGV  60
RLFPCLFCNK KFLKSQALGG HQNAHKKERS VGWNAHLYLP PPAADTASAS VAGGAAARAA  120
TTPVGSSHAL PMIQAVSHSC HHHEHHHRDG GAAAPLLETA WWSSCAEEKQ QRHPVDLNLR  180
L                                                                  181

SEQ ID NO: 3            moltype = DNA  length = 23
FEATURE                 Location/Qualifiers
source                  1..23
                        mol_type = other DNA
                        organism = synthetic construct
SEQUENCE: 3
tgcacctgct tctgccacat ggc                                          23

SEQ ID NO: 4            moltype = DNA  length = 20
FEATURE                 Location/Qualifiers
source                  1..20
                        mol_type = other DNA
                        organism = synthetic construct
SEQUENCE: 4
ctgcacctgc ttctgccaca                                              20
```

```
SEQ ID NO: 5            moltype = DNA  length = 20
FEATURE                 Location/Qualifiers
source                  1..20
                        mol_type = other DNA
                        organism = synthetic construct
SEQUENCE: 5
aattaatgca gcgtcggaat                                          20

SEQ ID NO: 6            moltype = DNA  length = 20
FEATURE                 Location/Qualifiers
source                  1..20
                        mol_type = other DNA
                        organism = synthetic construct
SEQUENCE: 6
ctgtttgggc aaccgccatg                                          20

SEQ ID NO: 7            moltype = DNA  length = 23
FEATURE                 Location/Qualifiers
source                  1..23
                        mol_type = other DNA
                        organism = synthetic construct
SEQUENCE: 7
ggcaaccgcc atgagggcag ggc                                      23

SEQ ID NO: 8            moltype = DNA  length = 5348
FEATURE                 Location/Qualifiers
source                  1..5348
                        mol_type = genomic DNA
                        organism = Zea mays
SEQUENCE: 8
gtgacttgag agagagtgtg tgttccgtgt gttatttgtc gctcttgtcg cttggctttt  60
gcaatcgtgc tttcttcctt cccattctta ttctcaaggc acttgtaatc aaagcaagag  120
acactaagtt tgtagtggtc cttgtggggt ctaagtgacc catttgatta aggagaaagc  180
tcactcggtc taagtgaccg tttgagagag ggaaagggtt gaaatagacc cggtctttgt  240
gaccacctca acggggagta ggtttgcaag aaccgaacct cggtaaaaca aatcatcgtg  300
tcttgctctt tatttgctca cgatttgttt tgcgccctct ctctctcgga ctcgtctata  360
tttctaacgc taacctgact tatagttgtg cttaagttta taaatttcag atttgcctta  420
ttcacccccc ctctaggcga ctttcagcgc ggtactgcgg cgacgtagga aatttggcga  480
gaaattgtcg ttgctgcaat tagtttccat gcccaggaat ccagcgagca ccatccggta  540
gacactgtga gctccaatga agcttttcgg gaccgaaacg acatcaaggg cacggatcgg  600
cgatcacggt ctcttcctct gttatcgcgg cggcattcac tcgcccaccc ttacggcaat  660
ggtacccttg ggccaccggt tcatcgtgat gcaagatgga tgagaggggg gggtgcacga  720
ctaggagtta tatatcctag gatctagctc aaatccgagc ggtgctagcc agatcggaga  780
agaacacgac agagtttgtt accggcaaag ggacccacgt ccaacgatcc atgagcacgc  840
gatgcactca aaggctacgg gcgggtccca ctggttggtc ttagccggat catgggtgcg  900
cgatgcatcg gcgaccgctt cctttcgtgt ggggaggctg ggtccgcgga cgaagaagtg  960
gaggtgggcc gggtagcggc ccacacgggc gaggggaagg aaaacagaat tgggctatgg  1020
aggaaggttt tggcccagcc agctgtttcc ttattttttta ttgatttctg ttttaaattt  1080
tcaactttaa attcaaatct cgaatttcaa attgtatttg ggtggaaaac tagaatctag  1140
ataaatgcac aatcaaataa atactcaaca tgatgcatat ttctatttat atatttttat  1200
agtaattgtt taatcctttt ggttaaataa catgcttcga aatatgccat acaacaattt  1260
tcagttttga agaaatatta atttaaacct atagtcaaat gaaaggttta tccaagattt  1320
attaattgtt tgttgtaata ggagatatat atattctcca attacaaggt gcttttgact  1380
taaccttatt tagagaaggt tttctagtca tacaattcat caattattaa ttgtagacat  1440
ccctgcttta tttctttgag aaaataaaac ctaatttcct agggttaaat ataataattt  1500
tttagatcac tatttatcca aaaaaatcat tgttatagat attttaatta ttgtttttga  1560
agaaatattt ataaattcca aaataaaatt ttggatgtta cgttggtgca ctggcctggg  1620
ccacgcacct tgctaaaacc ggcctgggcc gatttctttg ttccccgcac aatataatca  1680
cgagcatagg ctggcctcac tcgtctctaa acaggccggt tctcttcaaa catcgtaatt  1740
ttgaccccaa attggatccc tttcatttat atatgatgtt ttaatccgac ttttgacttc  1800
cagattattt tttgctgtca acaatcctag ctccagctgt catttatcca aaggtttatg  1860
gtggcagatc ttaacggctg gcatacgtgc agaatttctc ctttctttac agttacaccc  1920
ctcccctccc cctcgtgtcg gggagtgtgc agtgcacatc tgatgtgtat aaataatcac  1980
acgcacctat gcccactcca cctcccgcgt tcctccactc cacggctccc ccaccccact  2040
catcacactc tcccaccgca cctcgccgcc gcggggcacc gcgccataaa gtgcgttccc  2100
ggctgcacgg acgtcgagga gcagctcgca agtgtttctt ggtgcgtcga tcggcaagat  2160
gatcaccggc acggacttct accacgtcat gacggccatg gtgccgttgt acgttgccat  2220
gatcctggcg tacggatccg tcaggtggtg gcgcatcttc acgccggacc agtgctcggg  2280
gatcaaccgc ttcgtggcgc tcttcgccgt gccgctgctg tccttccact tcatctccac  2340
caacaacccc tacaccatga acatccggtt catcgccgcc gacacgctgc agaagctgat  2400
cgtcctggcg ctgctcactg catggagcta cctctcccgc cggggctgcc tcgagtggac  2460
catcacgctc ttctccctgt cgacgctgcc caacacgctg gtgatgggca tcccgctgct  2520
caagggcatg tacggcgact tctccggcag cctcatggtg cagatcgtgg tgctccagtg  2580
catcatctgg tacacgctga tgctgttcat gttcgagtac cgcggcgcca ggatcctcat  2640
caccgagcag ttccccgaca cggcgggcgc catcgcctcc atcgtggtgg accccgacgt  2700
ggtgtcgctg gacgggcgca acgacgccat cgagacggag gccgaggtga aggaggacgg  2760
caagatacac gtcaccgtgc ggcgctccaa cgcgtcgcgc tcggacatct actcccggcg  2820
gtccatgggg ttctccagca ccacgccgcg gcccagcaac ctgaccaacg ccgagatcta  2880
ctcgctgcag tcgtcgagga accccacgcc gcggggctcc agcttcaacc acaccgactt  2940
```

```
ctactccatg gtcggccgca gctccaactt cgccgccggg gacgcgttcg gcctgcgcac  3000
gggcgccacg cccaggccgt ccaactacga ggaggacccg cagggcaagg cgaacaagta  3060
cggccagtac ccggcgccca acccggccat ggcggcgcag cccgccaagg gcctcaagaa  3120
ggcggccaat gggcaggcca agggcgagga cggcaaggac ctacacatgt tcgtgtggag  3180
ctccagcgcg tcgcccgtgt ccgacgtgtt cggcaatggc gccgccgagt acaacgacgc  3240
ggccgccgtc aaggaggtcc gcatggccgt cgcctccccg cgcaaaggta gcttctcctc  3300
gtttttggct tttgagctcc ttccttcctg ctttggctgc gctgcatgct cagacacaca  3360
cctgttctgt tcttgttgga cgttttagtt gcggcggacg ggaggaagga gcggggcgag  3420
gacttcgcgg agcgggacga cttcagcttc gggaacaggg gcgcggcgga gagggacgcg  3480
gaagccggcg acgagaaggc ggcggcggcg gctgcggctg cgcaggggaa tgcaggcgcc  3540
gtggcggcgc ccgcggcgat gccaccgacg agcgtgatga cgcggctgat cctcatcatg  3600
gtgtggcgca aactcatccg taaccccaac acctactcca gcctcatcgg cctcatctgg  3660
tcgctcgtct gcttcaggta accagcgtca ccggcgcggc gtgcttgaaa ttagtagtgg  3720
gcgttgcatc tttcgctaac ctgtttcgtt tctggacacg aacgcatacg caggtggaac  3780
ttcgagatgc cggcgatcat cctcaagtcc atctcgatcc tctccgacgc cgggctcggc  3840
atggccatgt tcagcctcgg tccgtggatc tcaaaaccct ctctgctgcc tcctctgtct  3900
ggagtcgcat cgccacgcca cctatggaac agttaacccc cttgtactga caccgcgcgt  3960
gacgtcgcct tcctccgtgc agggctgttc atggcgctgc agccacggat aatcgcgtgc  4020
gggaacaagg tggccacgtt cgccatggcc gtgcggttcc tgaccggccc ggccgtcatg  4080
gccgccgcct cctttgccgt cggcctccgc ggcacgctcc tccacgtcgc catcgtccag  4140
gtaaaaactc tccgaaccga accgaaccaa accaaccaac cgcacaaaca aacccactgg  4200
caggcacgca cgccactgac aagggccgca ccgccttttg agaaagagat gaaaaaaaat  4260
atatccaagc acaagcagcg gtcaagtggc cggccgggca tgccgatcga tatgcccccct  4320
gtgccggtaa agcgcggcac agcctccttt cgcttttgga ctttgcacgc acaacacaaa  4380
ttcgcccttt tttttgttgc cccccccccc cccccccccc cccccccctc gccgcctctg  4440
ccactgactg acgttcgttt tgtttactga cgacgcacgc aggccgcgct gccgcagggc  4500
attgtcccct tcgtgttcgc caaggagtac ggcgtgcacc ctgacatcct cagcacggcg  4560
taagcaacgc agcctttgtg ttccatccgt cttgctcttg cttgcatgca gctgagctag  4620
gcactagcac tagcagcagc cagcagcagc agcgccggga ttcccgggtc tccgcccgct  4680
ttatttgcct cagggttttt tttttgtctc acctgctgtc ggctttgctt cgtcgtggtg  4740
ttgcagagtc atcttcggca tgctcatcgc gctgcccatc acgctggtgt actacatcct  4800
gatggggctg tgaaaaagcc agacaagctg ctcgttcccg caggccaaca gcgatgccgg  4860
atggggatgt ggagcaggag gagacagact agggggggaca agacaactgc gcaggggcag  4920
gggcgggggc ggggggcggc aggttaattc gtaggagtat gcttttaggt gtagacatca  4980
tggaacgcga ttagagagca aacaaaaaat gtttttagga caaacccaac gtcatatgca  5040
aaaatccttg ggggtgacag tttgcgttgc aaagcatccg gtcatgagtt ttgatttggg  5100
tgtgttaggg acttttcatg cgcatggctt tccatgccct atataaaatg gatgcgtgtc  5160
acttcgatgg aatgctaggg ctcttctttc ttgttcatct agggtatata tacttcttgg  5220
actggcacca cgcatgtccc tgcttcagta cttgcttaac agtatctgac atcaaagcgg  5280
gcgagtgggg tgatttggtc gttaatcctt cagcatcaaa cccttgctgt gcaaccgtac  5340
tagttcga                                                           5348
```

```
SEQ ID NO: 9           moltype = AA  length = 601
FEATURE                Location/Qualifiers
source                 1..601
                       mol_type = protein
                       organism = Zea mays
SEQUENCE: 9
MITGTDFYHV MTAMVPLYVA MILAYGSVRW WRIFTPDQCS GINRFVALFA VPLLSFHFIS  60
TNNPYTMNIR FIAADTLQKL IVLALLTAWS YLSRRGCLEW TITLFSLSTL PNTLVMGIPL  120
LKGMYGDFSG SLMVQIVVLQ CIIWYTLMLF MFEYRGARIL ITEQFPDTAG AIASIVVDPD  180
VVSLDGRNDA IETEAEVKED GKIHVTVRRS NASRSDIYSR RSMGFSSTTP RPSNLTNAEI  240
YSLQSSRNPT PRGSSFNHTD FYSMVGRSSN FAAGDAFGLR TGATPRPSNY EEDPQGKANK  300
YGQYPAPNPA MAAQPAKGLK KAANGQAKGE DGKDLHMFVW SSSASPVSDV FGNGAAEYND  360
AAAVKEVRMA VASPRKVAAD GRKERGEDFA ERDDFSFGNR GAAERDAEAG DEKAAAAAAA  420
AQGNAGAVAA PAAMPPTSVM TRLILIMVWR KLIRNPNTYS SLIGLIWSLV CFRWNFEMPA  480
IILKSISILS DAGLGMAMFS LGLFMALQPR IIACGNKVAT FAMAVRFLTG PAVMAAASFA  540
VGLRGTLLHV AIVQAALPQG IVPFVFAKEY GVHPDILSTA VIFGMLIALP ITLVYYILMG  600
L                                                                  601
```

```
SEQ ID NO: 10          moltype = DNA  length = 20
FEATURE                Location/Qualifiers
source                 1..20
                       mol_type = other DNA
                       organism = synthetic construct
SEQUENCE: 10
actgcacact ccccgacacg                                              20
```

```
SEQ ID NO: 11          moltype = DNA  length = 23
FEATURE                Location/Qualifiers
source                 1..23
                       mol_type = other DNA
                       organism = synthetic construct
SEQUENCE: 11
cagttacacc cctcccctcc ccc                                          23
```

```
SEQ ID NO: 12          moltype = DNA  length = 20
FEATURE                Location/Qualifiers
```

```
source                  1..20
                        mol_type = other DNA
                        organism = synthetic construct
SEQUENCE: 12
acctttggat aaatgacagc                                              20

SEQ ID NO: 13           moltype = DNA  length = 23
FEATURE                 Location/Qualifiers
source                  1..23
                        mol_type = other DNA
                        organism = synthetic construct
SEQUENCE: 13
ctgtcaacaa tcctagctcc agc                                          23

SEQ ID NO: 14           moltype = DNA  length = 23
FEATURE                 Location/Qualifiers
source                  1..23
                        mol_type = other DNA
                        organism = synthetic construct
SEQUENCE: 14
accccaaatt ggatcccttt cat                                          23

SEQ ID NO: 15           moltype = DNA  length = 20
FEATURE                 Location/Qualifiers
source                  1..20
                        mol_type = other DNA
                        organism = synthetic construct
SEQUENCE: 15
taaatgaaag ggatccaatt                                              20

SEQ ID NO: 16           moltype = DNA  length = 36
FEATURE                 Location/Qualifiers
source                  1..36
                        mol_type = other DNA
                        organism = synthetic construct
SEQUENCE: 16
gtaagcgctt acgtaagcgc ttacgtaagc gcttac                            36

SEQ ID NO: 17           moltype = DNA  length = 12
FEATURE                 Location/Qualifiers
source                  1..12
                        mol_type = other DNA
                        organism = synthetic construct
SEQUENCE: 17
gtaagcgctt ac                                                      12

SEQ ID NO: 18           moltype = DNA  length = 36
FEATURE                 Location/Qualifiers
source                  1..36
                        mol_type = other DNA
                        organism = synthetic construct
modified_base           1
                        mod_base = OTHER
                        note = 5' phosphorylation
modified_base           1^2
                        mod_base = OTHER
                        note = phosphorothioate bond
modified_base           2^3
                        mod_base = OTHER
                        note = phosphorothioate bond
modified_base           34^35
                        mod_base = OTHER
                        note = phosphorothioate bond
modified_base           35^36
                        mod_base = OTHER
                        note = phosphorothioate bond
SEQUENCE: 18
gtaagcgctt acgtaagcgc ttacgtaagc gcttac                            36

SEQ ID NO: 19           moltype =   length =
SEQUENCE: 19
000

SEQ ID NO: 20           moltype =   length =
SEQUENCE: 20
000
```

```
SEQ ID NO: 21          moltype =   length =
SEQUENCE: 21
000

SEQ ID NO: 22          moltype = DNA  length = 10
FEATURE                Location/Qualifiers
source                 1..10
                       mol_type = other DNA
                       organism = synthetic construct
SEQUENCE: 22
gacacgtaga                                                         10

SEQ ID NO: 23          moltype = DNA  length = 14
FEATURE                Location/Qualifiers
source                 1..14
                       mol_type = other DNA
                       organism = synthetic construct
SEQUENCE: 23
ttdccwwwww wggh                                                    14

SEQ ID NO: 24          moltype = DNA  length = 11
FEATURE                Location/Qualifiers
source                 1..11
                       mol_type = other DNA
                       organism = synthetic construct
SEQUENCE: 24
ccatttttag t                                                       11

SEQ ID NO: 25          moltype = DNA  length = 10
FEATURE                Location/Qualifiers
source                 1..10
                       mol_type = other DNA
                       organism = synthetic construct
SEQUENCE: 25
ccatttttgg                                                         10

SEQ ID NO: 26          moltype = DNA  length = 18
FEATURE                Location/Qualifiers
source                 1..18
                       mol_type = other DNA
                       organism = synthetic construct
SEQUENCE: 26
nttdccwwww nnggwaan                                                18

SEQ ID NO: 27          moltype = DNA  length = 18
FEATURE                Location/Qualifiers
source                 1..18
                       mol_type = other DNA
                       organism = synthetic construct
SEQUENCE: 27
nnwnccawww wtrgwwan                                                18

SEQ ID NO: 28          moltype = DNA  length = 16
FEATURE                Location/Qualifiers
source                 1..16
                       mol_type = other DNA
                       organism = synthetic construct
SEQUENCE: 28
ttwcyawwww trgwaa                                                  16

SEQ ID NO: 29          moltype = DNA  length = 10
FEATURE                Location/Qualifiers
source                 1..10
                       mol_type = other DNA
                       organism = synthetic construct
SEQUENCE: 29
ccatttttag                                                         10

SEQ ID NO: 30          moltype =   length =
SEQUENCE: 30
000

SEQ ID NO: 31          moltype =   length =
SEQUENCE: 31
000
```

```
SEQ ID NO: 32           moltype =   length =
SEQUENCE: 32
000

SEQ ID NO: 33           moltype =   length =
SEQUENCE: 33
000

SEQ ID NO: 34           moltype =   length =
SEQUENCE: 34
000

SEQ ID NO: 35           moltype =   length =
SEQUENCE: 35
000

SEQ ID NO: 36           moltype =   length =
SEQUENCE: 36
000

SEQ ID NO: 37           moltype =   length =
SEQUENCE: 37
000

SEQ ID NO: 38           moltype = DNA  length = 10
FEATURE                 Location/Qualifiers
source                  1..10
                        mol_type = other DNA
                        organism = synthetic construct
SEQUENCE: 38
ccwwwwwwgg                                                         10

SEQ ID NO: 39           moltype = DNA  length = 18
FEATURE                 Location/Qualifiers
source                  1..18
                        mol_type = other DNA
                        organism = synthetic construct
SEQUENCE: 39
gtttacataa atggaaaa                                                18

SEQ ID NO: 40           moltype = DNA  length = 18
FEATURE                 Location/Qualifiers
source                  1..18
                        mol_type = other DNA
                        organism = synthetic construct
SEQUENCE: 40
cttacctttc atggatta                                                18

SEQ ID NO: 41           moltype = DNA  length = 18
FEATURE                 Location/Qualifiers
source                  1..18
                        mol_type = other DNA
                        organism = synthetic construct
SEQUENCE: 41
ctttccattt ttagtaac                                                18

SEQ ID NO: 42           moltype =   length =
SEQUENCE: 42
000

SEQ ID NO: 43           moltype =   length =
SEQUENCE: 43
000

SEQ ID NO: 44           moltype =   length =
SEQUENCE: 44
000

SEQ ID NO: 45           moltype = DNA  length = 10
FEATURE                 Location/Qualifiers
source                  1..10
                        mol_type = other DNA
                        organism = synthetic construct
SEQUENCE: 45
aaacaatcta                                                         10
```

```
SEQ ID NO: 46           moltype = DNA  length = 15
FEATURE                 Location/Qualifiers
source                  1..15
                        mol_type = other DNA
                        organism = synthetic construct
SEQUENCE: 46
aaaaaaaatc tatga                                                   15

SEQ ID NO: 47           moltype =   length =
SEQUENCE: 47
000

SEQ ID NO: 48           moltype =   length =
SEQUENCE: 48
000

SEQ ID NO: 49           moltype =   length =
SEQUENCE: 49
000

SEQ ID NO: 50           moltype =   length =
SEQUENCE: 50
000

SEQ ID NO: 51           moltype =   length =
SEQUENCE: 51
000

SEQ ID NO: 52           moltype = DNA  length = 23
FEATURE                 Location/Qualifiers
source                  1..23
                        mol_type = other DNA
                        organism = synthetic construct
SEQUENCE: 52
ttcaaggggg catgtatctt gaa                                          23

SEQ ID NO: 53           moltype = DNA  length = 29
FEATURE                 Location/Qualifiers
source                  1..29
                        mol_type = other DNA
                        organism = synthetic construct
SEQUENCE: 53
ggattcaagg gggcatgtat cttgaatcc                                    29

SEQ ID NO: 54           moltype = DNA  length = 11
FEATURE                 Location/Qualifiers
source                  1..11
                        mol_type = other DNA
                        organism = synthetic construct
SEQUENCE: 54
taagagccgc c                                                       11

SEQ ID NO: 55           moltype =   length =
SEQUENCE: 55
000

SEQ ID NO: 56           moltype =   length =
SEQUENCE: 56
000

SEQ ID NO: 57           moltype =   length =
SEQUENCE: 57
000

SEQ ID NO: 58           moltype =   length =
SEQUENCE: 58
000

SEQ ID NO: 59           moltype =   length =
SEQUENCE: 59
000

SEQ ID NO: 60           moltype =   length =
SEQUENCE: 60
000

SEQ ID NO: 61           moltype = DNA  length = 15
FEATURE                 Location/Qualifiers
```

```
source                1..15
                      mol_type = other DNA
                      organism = synthetic construct
SEQUENCE: 61
tgtgtggtta atatg                                                       15

SEQ ID NO: 62         moltype =   length =
SEQUENCE: 62
000

SEQ ID NO: 63         moltype =   length =
SEQUENCE: 63
000

SEQ ID NO: 64         moltype =   length =
SEQUENCE: 64
000

SEQ ID NO: 65         moltype = DNA  length = 10
FEATURE               Location/Qualifiers
source                1..10
                      mol_type = other DNA
                      organism = synthetic construct
SEQUENCE: 65
cgtcaatgaa                                                             10

SEQ ID NO: 66         moltype = DNA  length = 13
FEATURE               Location/Qualifiers
source                1..13
                      mol_type = other DNA
                      organism = synthetic construct
SEQUENCE: 66
catacgtcgt caa                                                         13

SEQ ID NO: 67         moltype =   length =
SEQUENCE: 67
000

SEQ ID NO: 68         moltype = DNA  length = 10
FEATURE               Location/Qualifiers
source                1..10
                      mol_type = other DNA
                      organism = synthetic construct
SEQUENCE: 68
acgtcataga                                                             10

SEQ ID NO: 69         moltype = DNA  length = 10
FEATURE               Location/Qualifiers
source                1..10
                      mol_type = other DNA
                      organism = synthetic construct
SEQUENCE: 69
tctacgtcac                                                             10

SEQ ID NO: 70         moltype =   length =
SEQUENCE: 70
000

SEQ ID NO: 71         moltype = DNA  length = 12
FEATURE               Location/Qualifiers
source                1..12
                      mol_type = other DNA
                      organism = synthetic construct
SEQUENCE: 71
tctaacctac ca                                                          12

SEQ ID NO: 72         moltype =   length =
SEQUENCE: 72
000

SEQ ID NO: 73         moltype =   length =
SEQUENCE: 73
000

SEQ ID NO: 74         moltype =   length =
SEQUENCE: 74
000

SEQ ID NO: 75         moltype =   length =
```

```
SEQUENCE: 75
000

SEQ ID NO: 76          moltype =   length =
SEQUENCE: 76
000

SEQ ID NO: 77          moltype =   length =
SEQUENCE: 77
000

SEQ ID NO: 78          moltype = DNA  length = 26
FEATURE                Location/Qualifiers
source                 1..26
                       mol_type = other DNA
                       organism = synthetic construct
SEQUENCE: 78
atcttatgtc attgatgacg acctcc                                      26

SEQ ID NO: 79          moltype = DNA  length = 11
FEATURE                Location/Qualifiers
source                 1..11
                       mol_type = other DNA
                       organism = synthetic construct
SEQUENCE: 79
tacacttttg g                                                      11

SEQ ID NO: 80          moltype = DNA  length = 20
FEATURE                Location/Qualifiers
source                 1..20
                       mol_type = other DNA
                       organism = synthetic construct
SEQUENCE: 80
tgacgyaags rmtkacgymm                                             20

SEQ ID NO: 81          moltype =   length =
SEQUENCE: 81
000

SEQ ID NO: 82          moltype =   length =
SEQUENCE: 82
000

SEQ ID NO: 83          moltype = DNA  length = 20
FEATURE                Location/Qualifiers
source                 1..20
                       mol_type = other DNA
                       organism = synthetic construct
SEQUENCE: 83
ttggttttga tcaaaaccaa                                             20

SEQ ID NO: 84          moltype = DNA  length = 15
FEATURE                Location/Qualifiers
source                 1..15
                       mol_type = other DNA
                       organism = synthetic construct
SEQUENCE: 84
taattgactc aatta                                                  15

SEQ ID NO: 85          moltype =   length =
SEQUENCE: 85
000

SEQ ID NO: 86          moltype =   length =
SEQUENCE: 86
000

SEQ ID NO: 87          moltype =   length =
SEQUENCE: 87
000

SEQ ID NO: 88          moltype =   length =
SEQUENCE: 88
000

SEQ ID NO: 89          moltype =   length =
SEQUENCE: 89
000
```

```
SEQ ID NO: 90          moltype = DNA  length = 16
FEATURE                Location/Qualifiers
source                 1..16
                       mol_type = other DNA
                       organism = synthetic construct
SEQUENCE: 90
aggggcataa tggtaa                                           16

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
000

SEQ ID NO: 95          moltype = DNA  length = 16
FEATURE                Location/Qualifiers
source                 1..16
                       mol_type = other DNA
                       organism = synthetic construct
SEQUENCE: 95
aaaacagaat aggaaa                                           16

SEQ ID NO: 96          moltype =   length =
SEQUENCE: 96
000

SEQ ID NO: 97          moltype =   length =
SEQUENCE: 97
000

SEQ ID NO: 98          moltype =   length =
SEQUENCE: 98
000

SEQ ID NO: 99          moltype = DNA  length = 12
FEATURE                Location/Qualifiers
source                 1..12
                       mol_type = other DNA
                       organism = synthetic construct
SEQUENCE: 99
ccaatttaat gg                                               12

SEQ ID NO: 100         moltype =   length =
SEQUENCE: 100
000

SEQ ID NO: 101         moltype = DNA  length = 19
FEATURE                Location/Qualifiers
source                 1..19
                       mol_type = other DNA
                       organism = synthetic construct
SEQUENCE: 101
cttaaaccct aggggtaat                                        19

SEQ ID NO: 102         moltype = DNA  length = 10
FEATURE                Location/Qualifiers
source                 1..10
                       mol_type = other DNA
                       organism = synthetic construct
SEQUENCE: 102
ttwtactagt                                                  10

SEQ ID NO: 103         moltype =   length =
SEQUENCE: 103
000

SEQ ID NO: 104         moltype =   length =
SEQUENCE: 104
000
```

```
SEQ ID NO: 105          moltype =   length =
SEQUENCE: 105
000

SEQ ID NO: 106          moltype = DNA  length = 10
FEATURE                 Location/Qualifiers
source                  1..10
                        mol_type = other DNA
                        organism = synthetic construct
SEQUENCE: 106
ttgcatgact                                                        10

SEQ ID NO: 107          moltype =   length =
SEQUENCE: 107
000

SEQ ID NO: 108          moltype =   length =
SEQUENCE: 108
000

SEQ ID NO: 109          moltype =   length =
SEQUENCE: 109
000

SEQ ID NO: 110          moltype =   length =
SEQUENCE: 110
000

SEQ ID NO: 111          moltype =   length =
SEQUENCE: 111
000

SEQ ID NO: 112          moltype =   length =
SEQUENCE: 112
000

SEQ ID NO: 113          moltype = DNA  length = 34
FEATURE                 Location/Qualifiers
source                  1..34
                        mol_type = other DNA
                        organism = synthetic construct
SEQUENCE: 113
ccgacaaaag gccgacaaaa ggccgacaaa aggt                             34

SEQ ID NO: 114          moltype = DNA  length = 34
FEATURE                 Location/Qualifiers
source                  1..34
                        mol_type = other DNA
                        organism = synthetic construct
SEQUENCE: 114
accttttgtc ggccttttgt cggccttttg tcgg                             34

SEQ ID NO: 115          moltype = DNA  length = 68
FEATURE                 Location/Qualifiers
source                  1..68
                        mol_type = other DNA
                        organism = synthetic construct
SEQUENCE: 115
gccgacaaaa ggccgacaaa aggccgacaa aaggccgaca aaaggccgac aaaaggccga  60
caaaaggt                                                          68

SEQ ID NO: 116          moltype = DNA  length = 68
FEATURE                 Location/Qualifiers
source                  1..68
                        mol_type = other DNA
                        organism = synthetic construct
SEQUENCE: 116
accttttgtc ggccttttgt cggccttttg tcggcctttt gtcggccttt tgtcggcctt  60
ttgtcggc                                                          68

SEQ ID NO: 117          moltype = DNA  length = 100
FEATURE                 Location/Qualifiers
source                  1..100
                        mol_type = other DNA
                        organism = synthetic construct
SEQUENCE: 117
ccgacaaaag gccgacaaaa ggccgacaaa aggccgacaa aaggccgaca aaaggccgac  60
aaaaggccga caaaaggccg acaaaaggcc gacaaaaggt                       100
```

-continued

```
SEQ ID NO: 118          moltype = DNA  length = 100
FEATURE                 Location/Qualifiers
source                  1..100
                        mol_type = other DNA
                        organism = synthetic construct
SEQUENCE: 118
accttttgtc ggccttttgt cggccttttg tcggcctttt gtcggccttt tgtcggcctt  60
ttgtcggcct tttgtcggcc ttttgtcggc cttttgtcgg                        100

SEQ ID NO: 119          moltype = DNA  length = 16
FEATURE                 Location/Qualifiers
source                  1..16
                        mol_type = other DNA
                        organism = synthetic construct
SEQUENCE: 119
acgtaagcgc ttacgt                                                  16

SEQ ID NO: 120          moltype = DNA  length = 43
FEATURE                 Location/Qualifiers
source                  1..43
                        mol_type = other DNA
                        organism = synthetic construct
SEQUENCE: 120
aagagatgag ctcttgagca atgtaaaggg tcaagttgtt tct                    43

SEQ ID NO: 121          moltype = DNA  length = 43
FEATURE                 Location/Qualifiers
source                  1..43
                        mol_type = other DNA
                        organism = synthetic construct
SEQUENCE: 121
agaaacaact tgaccettta cattgctcaa gagctcatct ctt                    43

SEQ ID NO: 122          moltype = DNA  length = 19
FEATURE                 Location/Qualifiers
source                  1..19
                        mol_type = other DNA
                        organism = synthetic construct
SEQUENCE: 122
accgcggccg cggccgcgg                                               19

SEQ ID NO: 123          moltype = DNA  length = 38
FEATURE                 Location/Qualifiers
source                  1..38
                        mol_type = other DNA
                        organism = synthetic construct
SEQUENCE: 123
tcggtccgac aaaaggccga caaaaggcgg acaaaagg                          38

SEQ ID NO: 124          moltype = DNA  length = 38
FEATURE                 Location/Qualifiers
source                  1..38
                        mol_type = other DNA
                        organism = synthetic construct
SEQUENCE: 124
accgaccttt tgtcggcctt ttgtcggcct tttgtcgg                          38

SEQ ID NO: 125          moltype =   length =
SEQUENCE: 125
000
```